US00RE44883E

(19) United States
(12) Reissued Patent
Cha

(10) Patent Number: US RE44,883 E
(45) Date of Reissued Patent: May 6, 2014

(54) SURGICAL INSTRUMENT FOR ORTHOPEDIC SURGERY

(71) Applicant: Charles W. Cha, Marietta, GA (US)

(72) Inventor: Charles W. Cha, Marietta, GA (US)

(73) Assignee: Spinascope, Inc., Cartersville, GA (US)

(21) Appl. No.: 13/873,364

(22) Filed: Apr. 30, 2013

Related U.S. Patent Documents

Reissue of:

(64) Patent No.: 8,221,424
Issued: Jul. 17, 2012
Appl. No.: 12/553,471
Filed: Sep. 3, 2009

U.S. Applications:

(63) Continuation-in-part of application No. 11/017,150, filed on Dec. 20, 2004, now Pat. No. 7,585,300.

(60) Provisional application No. 60/531,209, filed on Dec. 19, 2003.

(51) Int. Cl.
*A61B 17/32* (2006.01)

(52) U.S. Cl.
USPC ..... 606/80

(58) Field of Classification Search
USPC ..... 606/7, 80, 84, 85, 170, 180; 451/358, 451/451; 433/125, 130, 144
See application file for complete search history.

(56) References Cited

U.S. PATENT DOCUMENTS

| | | | |
|---|---|---|---|
| 2,429,356 | A | 10/1947 | Hicks |
| 4,445,509 | A | 5/1984 | Auth |
| 4,466,429 | A | 8/1984 | Loscher et al. |
| 4,541,423 | A | 9/1985 | Barber |
| 4,646,738 | A | 3/1987 | Trott |
| 5,138,797 | A | 8/1992 | Siden |
| 5,411,514 | A | 5/1995 | Fucci et al. |
| 5,620,447 | A | 4/1997 | Smith et al. |
| 5,695,513 | A | 12/1997 | Johnson et al. |
| 5,807,241 | A | 9/1998 | Heimberger |
| 5,851,208 | A | 12/1998 | Trott |
| 5,851,212 | A | 12/1998 | Zirps et al. |
| 5,938,678 | A | 8/1999 | Zirps et al. |
| 6,053,907 | A | 4/2000 | Zirps |
| 6,077,287 | A | 6/2000 | Taylor et al. |
| 6,464,711 | B1 | 10/2002 | Emans et al. |
| RE38,335 | E | 11/2003 | Aust et al. |
| 6,645,218 | B1 | 11/2003 | Cassidy et al. |
| 6,656,195 | B2 | 12/2003 | Peters et al. |
| 7,503,920 | B2 | 3/2009 | Siegal |
| 7,785,337 | B2 | 8/2010 | Adams et al. |
| 8,277,474 | B2 | 10/2012 | Norman et al. |

*Primary Examiner* — Pedro Philogene
*Assistant Examiner* — David Comstock
(74) *Attorney, Agent, or Firm* — Duane Morris LLP

(57) ABSTRACT

A rotatable surgical instrument having a protective hood with articulating bendable distal end is provided to improve and enable various orthopedic surgical procedures such as arthroscopy. The protective hood surrounds the surgical tool bit exposing only a portion of the tool bit for removing bone or soft tissue material and protects the nerve from the surgical tool bit. The protective hood can be controllably rotated from the instrument's hand piece to control the orientation of the attack angle of the surgical tool bit. Additionally, the bending of the distal end of the instrument can be controlled from the hand piece.

20 Claims, 33 Drawing Sheets

SURGICAL INSTRUMENT FOR ORTHOPEDIC SURGERY

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation-in-part application of the co-pending U.S. patent application Ser. No. 11/017,150 filed on Dec. 20, 2004, the contents of which is incorporated herein by reference.

FIELD OF THE INVENTION

This invention relates to a surgical instrument for use in orthopedic surgeries and more particularly to a surgical high-speed burr for use in spinal surgical procedures and soft tissue resectors useful in arthroscopy.

BACKGROUND OF THE INVENTION

Spinal stenosis is a degenerative condition of the spine that afflicts primarily the elderly population. Patients with lumbar spinal stenosis suffer from severe radiating pain, which limits their ability to ambulate and can cause weakness and numbness in the legs and in severe cases, loss of bowel and bladder control may occur. It is the development of hypertrophic bone spurs off the facet joints, protrusions of the disc annulus, as well as hypertrophy of the ligamentum flavum that combine to narrow the space available for the nerves in the spinal canal.

The standard surgical procedure to treat lumbar spinal stenosis is known as the lumbar laminectomy and foraminotomy. During this procedure, the surgeon removes the spinous processes, the interspinous ligaments and the central portion of the spinal lamina to gain a line of sight into the lateral recess and into the foramen so that the nerve compression can be relieved in these areas. The current standard tools for performing this procedure are the Kerrison punch and angled curettes and in severe instances, osteotomes. To remove the offending bone using these instruments, a surgeon places the instrument into the interval between the compressing bone and the underlying nerve that is being compressed and the bone is then removed from the dorsal aspect of the nerve where it is impinged, thereby relieving compression exerted on the spinal nerve. In situations where the compression on the nerve is not very severe, one can safely insert the Kerrison footplate or the curette into the interval between the nerve root and the surrounding bone to perform the necessary bone removal.

However, when there is a severe amount of compression at the neural foramen or the lateral recess, the interval between the nerve root and the encroaching bone may not be sufficient to safely conduct the neural decompression using the conventional tools, such as a Kerrison punch or a curette. Insertion of a Kerrison footplate or a curette into a severely stenotic interval may cause compressive injury to an already compressed nerve root. In these situations, the only conventionally available method of successfully decompressing the neural compression, especially in the foramen, has been to pass a small curved osteotome in the plane that is superior to the nerve root and osteotomize the bone that is encroaching on the nerve root from above. This maneuver, however, poses risk to the nerve root because there is a possibility that the osteotome will slip or advance too deep, thereby damaging the exiting nerve. Thus, there is a need for an improved instrument that would allow a safer, more controlled method of foraminal lateral recess decompression that minimizes risks to the nerve roots, especially in severely stenotic situations.

Additionally, the need to remove the interspinous ligament, the spinous processes and the central portion of the lamina in open lumbar laminectomy is only to allow the surgeon to have a line of sight into the lateral recess and foramen to remove pressure on the compressed nerve. In surgery, the surgeon works from the opposite side of the table to get the appropriate line of sight and angle of attack at the encroaching bone and soft tissue in the lateral recess in the foramen. Working from the contralateral side of the table is necessary in order to be able to undercut the facet joints and thereby preserve spinal stability with these procedures. This line of attack is necessary because of the shape of the current standard instruments, such as a Kerrison punch, curette or osteotome, and the necessary vector of applied force that is required using those instruments. There is therefore an additional need for an instrument that would allow for ipsilateral decompression of the lateral recess and the foramen. This instrument would need to allow for undercutting of the facet joints and removal of compressive bone and soft tissue in the lateral recess and the foramen on the ipsilateral side of the patient (decompression on the same side of the table as opposed to working across the spinal canal from the contralateral side of the table). Such an instrument would also allow for the application of minimally invasive techniques to perform lumbar decompressions and would allow for the maximal preservation of bone and ligaments thereby preserving spinal stability.

One tool that is available to a spine surgeon to remove bone, in a controlled fashion, is a high speed burr. The burr is used from the dorsal surface of the bone heading towards the neural elements and the bone is thinned down until it is wafer thin and can be picked away with curettes. If one is too aggressive with the burr, then neural injury can occur by penetrating the dura or wrapping the neural elements in the burr bit. Because the risk of catching the neural elements with the conventional high speed burr bit is too high, the use of conventional high speed burrs to perform the lateral recess and foraminal decompression has not been practicable. Thus, an improved novel high speed burr for removing bone in such tight spaces is desired.

SUMMARY

According to a preferred embodiment of the present disclosure, a surgical instrument comprises a hand piece having a distal end and a proximal end. A shaft portion extends from the distal end of the hand piece and has a distal end and a proximal end. A drive shaft is disposed for rotation within the shaft portion and the drive shaft has a distal end and a proximal end. A surgical tool bit is connected to the distal end of the drive shaft. A protective hood is connected to the distal end of the shaft portion, wherein the surgical tool bit resides within the protective hood, partially exposed, and the protective hood is rotatable relative to the surgical tool bit exposing a different portion of the surgical tool bit. The hand piece also includes a first control member that is operably connected to the proximal end of the shaft portion and manipulation of the first control member controls the rotation of the protective hood relative to the hand piece and the drive shaft via the shaft portion.

According to another embodiment, the surgical instrument also comprises an inner shaft disposed within the shaft portion and a tool-bit spindle housing disposed within the protective hood. The drive shaft is disposed for rotation within the inner shaft and the distal end of the drive shaft extends through the tool-bit spindle housing and connected to the surgical tool bit. A flexible neck portion connects the protective hood to the distal end of the shaft portion, wherein the flexible neck portion comprises an outer sleeve and an inner sleeve. The outer sleeve connects the distal end of the shaft and the protective hood. The inner sleeve has a ventral side and a dorsal side and connects the inner shaft to the tool-bit spindle housing. The inner sleeve is further configured and adapted to preferentially bend towards the ventral side. An actuating means is provided within the inner sleeve and the inner shaft for controllably bending the flexible neck portion. The drive shaft comprises a flexible portion extending through the flexible neck portion.

A surgical instrument according to an embodiment of the invention comprises a hand piece, a rigid shaft portion extending from the hand piece and having a distal end and a proximal end, and a drive shaft disposed for rotation within the shaft portion. The drive shaft has a distal end and a proximal end thereof and a surgical tool bit is connected to the distal end of the drive shaft. A protective hood including a dissecting foot plate portion is connected to the distal end of the shaft portion. And the surgical tool bit resides within the protective hood, partially exposed, and the protective hood is rotatable relative to the surgical tool bit along the longitudinal axis of the surgical tool bit, exposing a different portion of the surgical tool bit.

A surgical instrument according to another embodiment comprises a hand piece, a power drive mechanism provided within the hand piece, a rigid shaft portion extending from the hand piece and having a distal end and a proximal end, and a drive shaft disposed for rotation within the shaft portion. The drive shaft has a distal end and a proximal end thereof, and the proximal end is connected to the power drive mechanism. A surgical tool bit is connected to the distal end of the drive shaft and a protective hood including a dissecting foot plate portion is attached to the distal end of the shaft portion. The surgical tool bit resides within the protective hood, partially exposed, and the protective hood is rotatable relative to the surgical tool bit along the longitudinal axis of the tool bit, exposing a different portion of the surgical tool bit.

The dissecting soft tissue resector embodiment could also be used, with an extended kind of a Woodson type tip, to get in between compressive tissue and the nerve root that is sometimes found in the foramen that can continue to cause residual compression on the nerve, even after a dorsal bony decompression has been performed. The dissecting soft tissue resector may be used to debride annulus, ligamentum flavum, disc and or cartilage that are encroaching the nerve root in the axilla or in the foramen.

In addition to allowing a safer foraminal decompression in the open setting, the surgical instrument according to an embodiment of the invention is also suited for performing lumbar decompression in minimally invasive surgical settings while sparing bone and ligament that are in close proximity to the surgical site.

BRIEF DESCRIPTION OF THE DRAWING

The drawings are schematic and the like reference numerals used in the figures denote like parts throughout the various figures.

FIG. 1b is a detailed side elevational view of region A in FIG. 1a.

FIG. 1c is a front elevational view of the region A in FIG. 1a.

FIG. 2b is a front elevational view of the surgical instrument of FIG. 2a.

FIG. 3b is a front elevational view of the dissecting soft tissue resector of FIG. 3a.

FIG. 4b is a cross-sectional schematic illustration of the inner shaft member of FIG. 4a;

FIG. 5c is a cross-sectional schematic illustration of region B in FIG. 5a.

FIG. 6B is a plan view illustration of the surgical instrument of FIG. 6a. FIG. 7a is a more detailed view of the distal end of the surgical instrument of FIG. 6a.

FIG. 7b is a longitudinal sectional view of the distal end of the surgical instrument of FIG. 6a.

FIG. 8 is a longitudinal sectional view of the proximal end of the surgical instrument of FIG. 6a.

FIGS. 9a-9f are various illustrations of the flexible neck portion of the distal end of the surgical instrument of FIG. 6a.

FIG. 17b is an exploded view of the structure shown in FIG. 17a.

FIG. 18a is a detailed view of the flexible neck portion 1517 of the surgical instrument 1500 from the ventral side V of the surgical instrument 1500.

FIG. 18b is an exploded view of the structure shown in FIG. 18a.

DETAILED DESCRIPTION

Figure 1A:
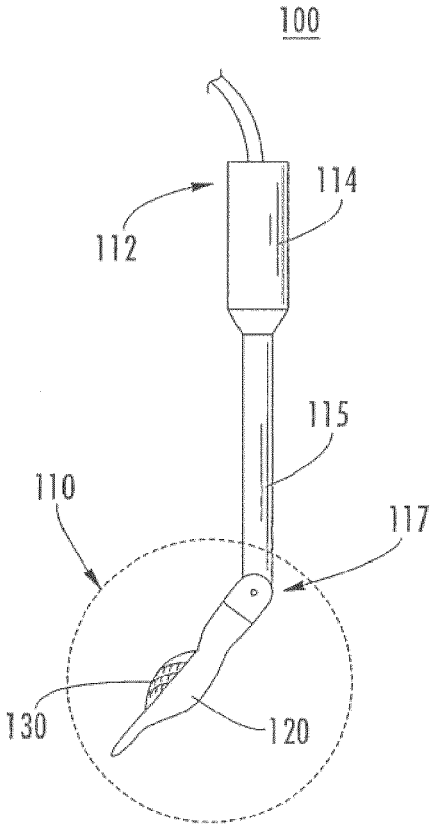
FIG. 1a is a side elevational view of a surgical instrument according to an embodiment of the invention.

Various embodiments of the dissecting high speed burr according to the invention will now be described in reference to the FIGS. 1 through 5. The embodiments illustrated in these drawings are presented as examples of various embodiments of the invention only. These illustrations are not meant to limit the invention to these examples. The illustrations are not to scale and, thus, the relative dimensions of some of the aspects of the instrument may be exaggerated.

Referring to FIGS. 1a-1d, a surgical instrument 100 according to an embodiment of the invention is disclosed. The surgical instrument 100 comprises a hand piece 114 at its proximal end 112 and a bone burring surgical tool bit, a burr bit 130, at its distal end 110 housed in a protective hood 120. A generally hollow outer tube 115 connects the hand piece 114 to the protective hood 120.

In an embodiment of the invention, the outer tube 115 may be angled at a region 117 near the distal end 110 to allow the instrument to reach into the neural foramen of a patient during a foraminal decompression. The angled region 117 may be configured and adapted to have a fixed angle or provided with a hinged or other articulated flexible joints to allow the angle of the distal end 110 of the instrument to be adjusted as desired.

In another embodiment, the outer tube 115 may be straight without any angled neck portion 117. Such straight burr instrument may not be suitable for foraminal decompression but could be used in situations where the bone spurs are encroaching the foramen from the posterior lip of the ventral vertebral bodies. The straight surgical instrument may be used to go in underneath a nerve root and remove the ventrally encroaching bone. Currently, there are no tools that allow for the safe removal of bone ventral to the nerve root in the foramen.

The hand piece 114 functions as a handle for the surgeon to hold and manipulate the surgical instrument 100 and may house a power drive mechanism, such as an electrical motor or a pneumatic drive mechanism, to drive a surgical tool bit 130 of the surgical instrument 100. The tool bit 130 also may be driven by other suitable driving means. An elongated outer tube 115 connects the hand piece 114 and the protective hood 120. The outer tube 115 houses an appropriate mechanical linkage that connects the power drive mechanism to the burr bit 130.

The protective housing 120 has an opening 122 exposing one portion of the tool bit 130. Generally, the superior or dorsally facing surface of the tool bit 130 is exposed while the undersurface of the tool bit 130 is protected by a protective hood 120. The protective hood 120 includes a dissecting foot plate portion 119, the portion of the protective hood 120 from about the widest portion to the distal tip 118, that is shaped to enable the distal end 110 of the surgical instrument 100 to be inserted between the encroaching bone and the nerve root during a foraminal decompression procedure, for example. The protective hood 120 enshrouding the tool bit 130 protects the surrounding soft tissue, such as the nerve root, from being damaged by the burr bit 130 during the bone burring procedure.

The dissecting foot plate 119 is shaped like a surgical dissection tool such as a curette, the Woodson, etc. During surgery, the distal end 110 of the surgical instrument 100 is placed in the neural foramen with the exposed tool bit 130 oriented towards the offending bone. The rest of the tool bit 130 is covered by the protective hood 120, which rests against the underlying nerve root thereby protecting the nerve from the tool bit 130.

Figure 1B:
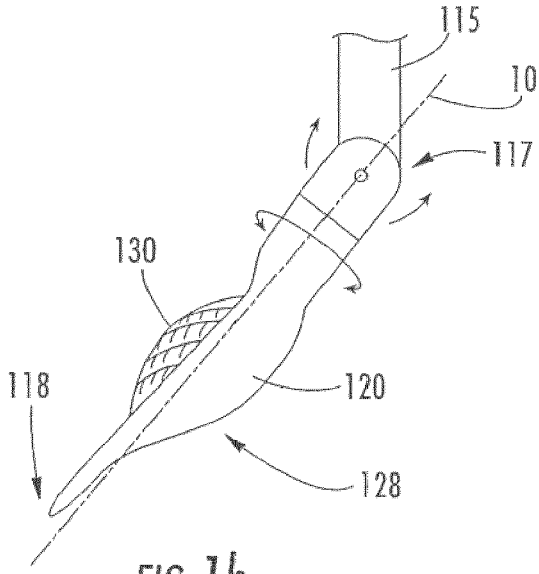
Figure 1C:
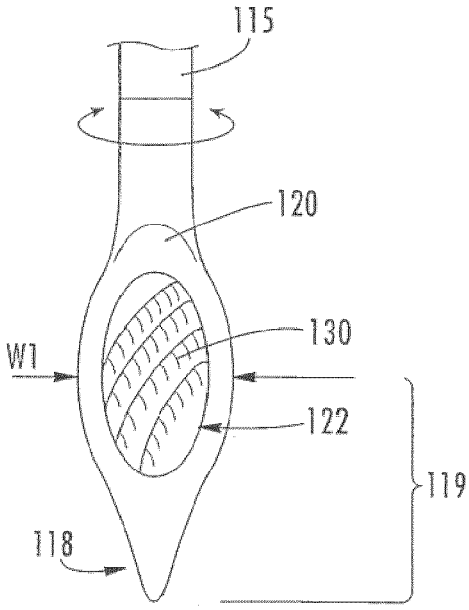

FIGS. 1b and 1c are detailed side view and a frontal view, respectively, of the distal end 110 of the surgical instrument 100. The protective hood 120 may be axially rotatably attached to the outer tube 115 so that the protective hood 120 is rotatable about a longitudinal axis 10 of the distal end 110 of the surgical instrument 100. The opening 122 of the protective hood 120 is sized and configured to expose a desired amount of the tool bit 130 appropriate for the bone removal to be performed with the instrument. By having an axially rotatable protective hood 120, the burr bit's exposed cutting portion can be repositioned to accommodate to the varying geometric relationship of the offending bone to the compressed nerve. In other words, the protective hood 120 may be axially rotated, changing the angle of attack of the tool bit 130. The surgical instrument 100 is mechanically configured such that the rotational motion of the protective hood 120 is manipulable by the surgeon from the hand piece 114. Thus, the surgeon can change the direction of the bone resection without moving the whole instrument, the surgical instrument 100, just by manipulating the orientation of the protective hood 120 from the hand piece 114.

Conversely, the protective hood 120 is positioned to maximally protect the underlying nerve from the exposed burr face. This configuration allows the angular orientation of the opening 122 in the protective hood 120 to be changed about its longitudinal axis and change the direction of the exposed burr bit.

Figure 1D:
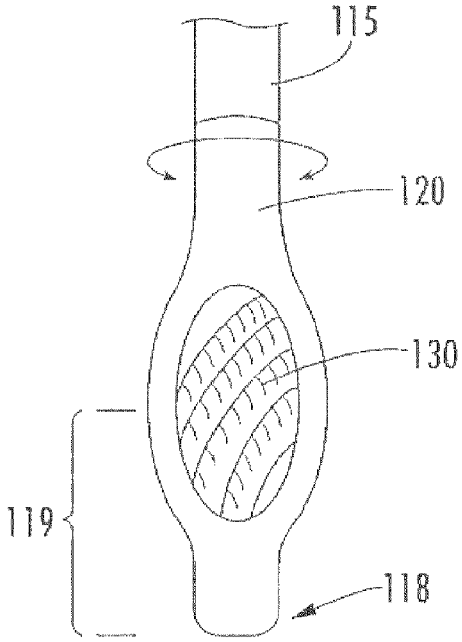
FIG. 1d is a front elevational view of the surgical instrument of FIG. 1c with an alternative shape for the dissecting foot plate according to another embodiment of the invention.
Figure 1E:
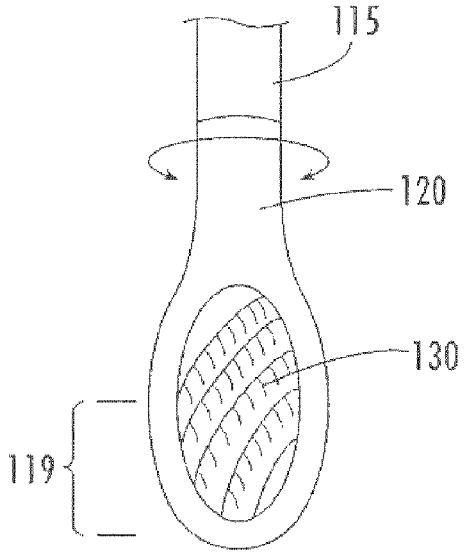
FIG. 1e is an illustration of a dissecting foot plate of a surgical instrument according to another embodiment.

The surgical tool bit 130, the protective hood 120 and the dissecting foot plate portion 119 of the surgical instrument 100 may be made in any desired sizes. In one embodiment, the protective hood 120 and the dissecting foot plate portion 119 may be provided in the following dimensions that are useful for foraminal decompression. In this example, the dissecting foot plate 119 of the instrument is illustrated with a shape resembling a Woodson tip. In FIGS. 1c and 1d, a surgical instrument having Woodson-type dissecting foot plate 119 according to an embodiment is disclosed. In FIG. 1e, a dissecting burr instrument having a curette-type dissecting foot plate 119 according to another embodiment is disclosed.

TABLE

| Burr Bit Diameter | 2 mm | | 3 mm | | 4 mm | |
|---|---|---|---|---|---|---|
| Protective Hood Size (diameter at the widest portion) | 3 mm | 8 mm | 4 mm | 9 mm | 5 mm | 10 mm |

TABLE-continued

| | |
|---|---|
| Dissecting Foot Plate Size | 1 to 8 mm long with taper depending on the width of the protective hood. |

The protective hood sizes are the diameter W1 (FIG. 1c) of the hood measured at the widest portion. In these examples, there are two sizes of protective hood 120 for each burr bit size. The larger diameter protective hoods are primarily intended for central laminectomy whereas the smaller protective hoods are primarily intended for foraminotomy. This preference is determined by the amount of protection needed for the nerve tissue depending on the type of procedure and the location in which the instrument is being used to remove bony tissues from the patient. Some procedures require more protection from the burr for the other tissues surrounding the surgical site.

During surgery, the surgeon inserts the dissecting foot plate portion 119 of the surgical instrument 100 into the interval between the nerve root and the overlying compressing bone and continue to insert the instrument into the interval until the burr is positioned at a suitable location for removing the encroaching bone. The surgical instrument 100 is then turned on at high speed and the tool bit 130 is generally pushed forward into the encroaching bone. As such the whole width of the surgical instrument 100 is not forced into the interval between the bone and the nerve root. This minimizes any additional compression that may be exerted by the surgical instrument 100 because as the burr is advanced, the overlying bone is resected. The amount of bone that is removed depends on the combined girth or the diameter of the tool bit 130 and the protective hood 120 that is inserted into the interval.

Figure 2A:
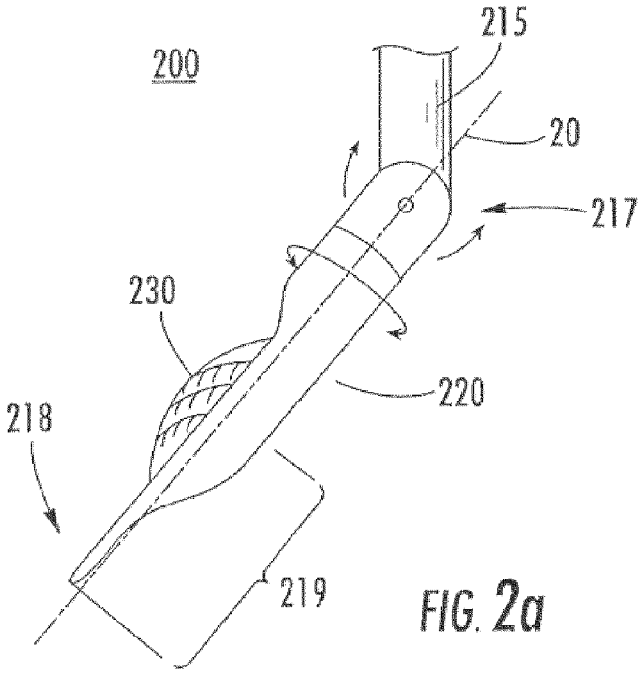
FIG. 2a is a side elevational view of the distal end of another surgical instrument according to another embodiment of the invention.

FIG. 2a is a schematic side view illustration of a surgical instrument 200 according to another embodiment of the invention. The surgical instrument 200 of this embodiment is similar to that illustrated in FIGS. 1a-1c. The surgical instrument 200 comprises an axially rotatable protective hood 220 that houses a burr bit 230. The protective hood 220 is axially rotatably attached to outer tube 215. The diameter of the outer tube 215 and the diameter of the rotating protective hood 220 are substantially similar throughout their lengths without the bulged portion 128 of the protective hood 120 in the embodiment of the surgical instrument 100. Such configuration provides smoother profile that may be beneficial during a surgical procedure.

Figure 2B:
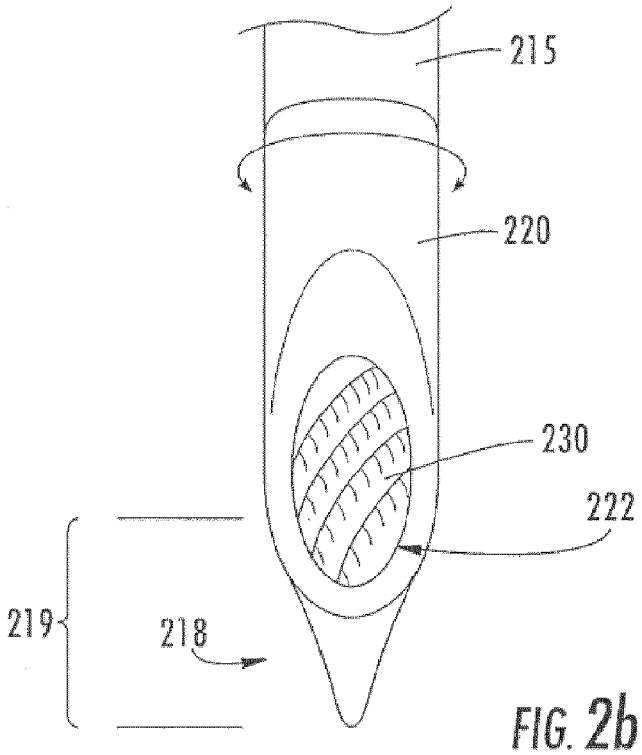

FIG. 2b is a schematic frontal view illustration of the surgical instrument of FIG. 2a. The protective hood 220 has an opening 222 exposing one portion of the burr bit 230. Generally, the superior or dorsally facing surface of the burr bit 230 is exposed while the undersurface of the burr bit 230 is protected by a protective hood 220. Again, the shape of the dissecting foot plate portion 219 of the protective hood 220 may be made in a variety of shapes as appropriate to meet the variety of dissecting action required in various spinal decompression procedures or any other bone removing procedures in which these instruments may be useful. For example, the dissecting foot plate portion 219 may be shaped like a curette or a Woodson surgical dissection tool.

Figure 2C:
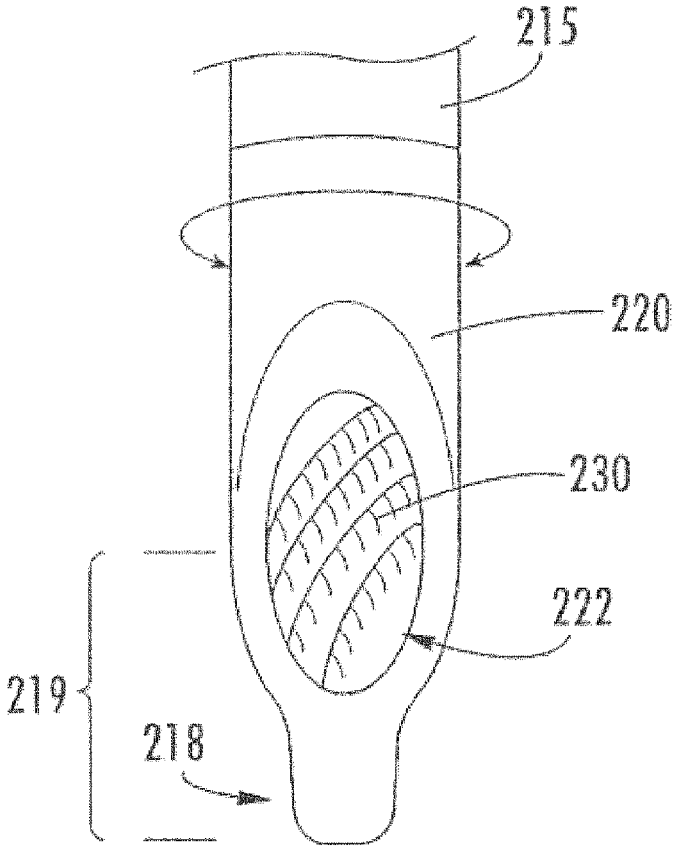
FIG. 2c is a front elevational view of the surgical instrument of FIG. 2b with an alternative shape for the dissecting foot plate according to another embodiment of the invention.

The protective hood 220 may be rotatable about the longitudinal axis 20 of the distal end of the instrument to allow the surgeon to change the direction of the burring action of the burr bit. The protective hood 220 will generally be fixed so that it does not rotate while the surgical instrument 200 is in operation (i.e. the burr bit is rotating). Adjustments in the orientation of the protective hood may be made when the instrument is turned off. In FIG. 2c, an alternative shape for the dissecting foot plate portion 219 is illustrated, which is a Woodson-type tip.

Figure 3A:
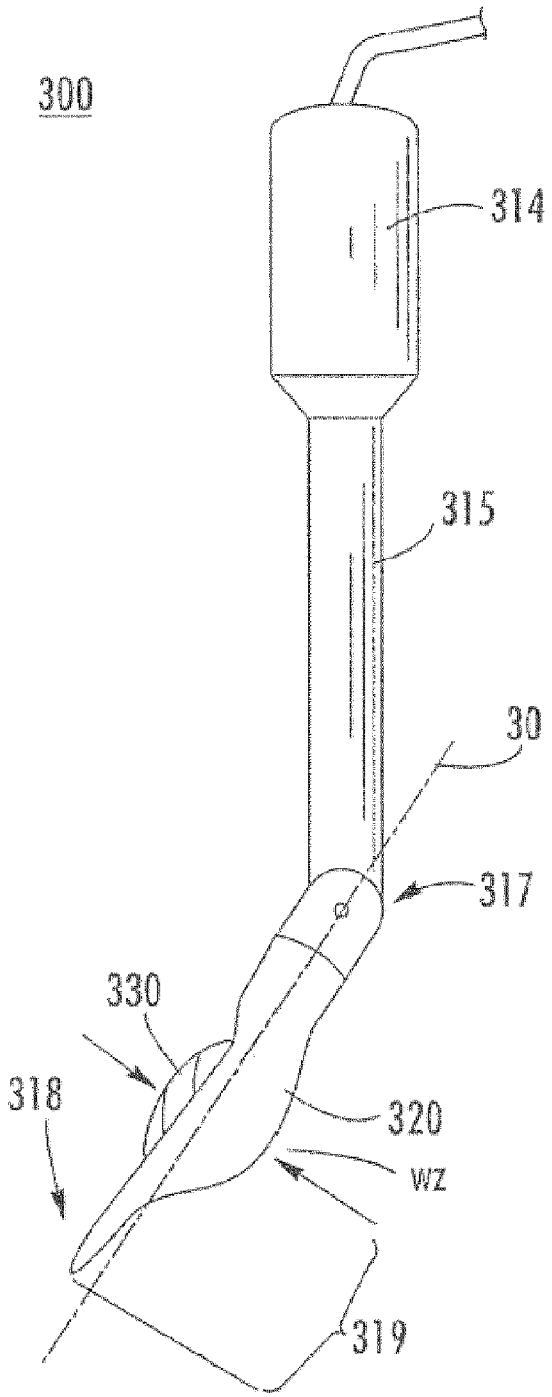
FIG. 3a is a side elevational view of a dissecting soft tissue resector according to another embodiment of the invention.
Figure 3B:
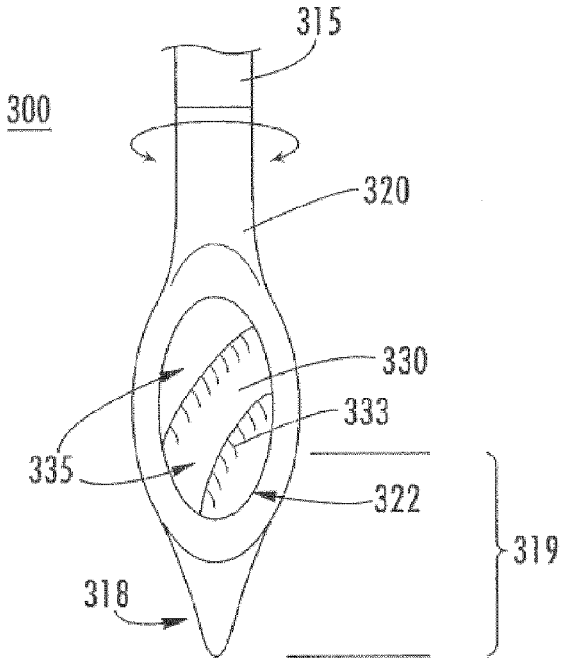
Figure 3C:
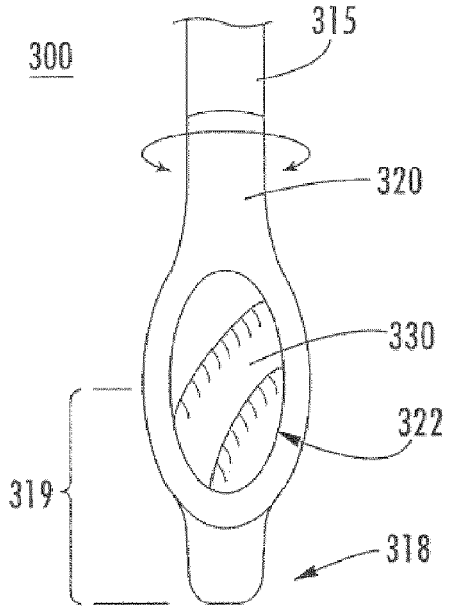
FIG. 3c is a front elevational view of the dissecting soft tissue resector of FIG. 3a having an alternative shaped dissecting foot plate according to another embodiment of the invention.

Referring to FIGS. 3a-3c, a dissecting soft tissue resector 300 according to another embodiment of the invention is disclosed. The dissecting soft tissue resector 300 comprises a hand piece 314 and an outer tube 315 that functions as the shaft of the soft tissue resector 300. In this embodiment, however, the surgical tool disposed within a rotating protective hood 320 is a soft tissue resector bit 330 rather than a burr bit 130, 230. The protective hood 320 has an opening 322 exposing a portion of the soft tissue resecting bit 330. The portion of the protective hood 320 between the widest portion W2 of the protective hood and the distal tip 318 of the protective hood 320 is a dissecting foot plate portion 319, shaped to resemble a surgical dissection tool, such as a curette or a Woodson. The outer tube 315 may be angled to allow the instrument to reach into the neural foramen or other surgical sites with ease.

The protective hood 320 may be axially rotatably attached to the outer tube 315. The protective hood 320 is rotatable about a longitudinal axis 30 of the distal end 310 of the dissecting soft tissue resector 300. The opening 322 is sized and configured to expose a desired amount of the soft tissue resecting bit 330 appropriate for the bone removal to be performed with the instrument. This rotatable attachment allows the soft tissue resecting bit's exposed cutting portion to be repositioned to accommodate the varying geometry at the surgical site. In other words, the protective hood 320 may be axially rotated, changing the angle of attack of the soft tissue resecting bit 330. The side with the exposed soft tissue resecting bit 330 would generally be the dorsal side of the soft tissue resector 300. The soft tissue resecting bit 330 is similar to that of the meniscal debriders that are used in arthroscopic surgery.

The dissecting soft tissue resector 300 may preferably have a suction means attached to it to remove the resected tissue debris from the surgical site. Vacuum may be drawn through the outer tube 315 and to the soft tissue resecting bit 330. Preferably, the tissue resecting bit's cutting teeth 333 are spaced apart to provide sufficiently large open spaces 335 between the cutting teeth 333, allowing removal of the resected tissue debris through those open spaces by the vacuum. The soft tissue resector 300 may be configured with channel(s) or passage(s) within the instrument so that vacuum may be applied through the instrument, the open spaces between the cutting teeth 333 of the soft tissue resector bit 330 functioning as the intake opening.

The dissecting soft tissue resector 300 embodiment could also be used, with an extended kind of a Woodson-type foot plate portion 319 as shown in FIGS. 3b and 3c, to get in between compressive tissue and the nerve root that is sometimes found in the foramen that can continue to cause residual compression on the nerve, even after a dorsal bony decompression has been performed. The dissecting soft tissue resector may be used to debride annulus, ligamentum flavum, disc and or cartilage that are encroaching the nerve root in the axilla or in the foramen.

Figure 4A:
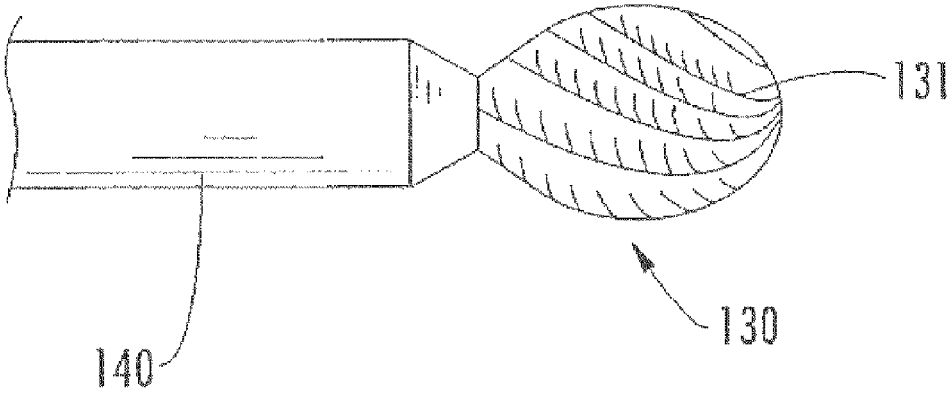
FIG. 4a is a side elevational view of an inner shaft member of the surgical instrument of FIG. 1.
Figure 4B:
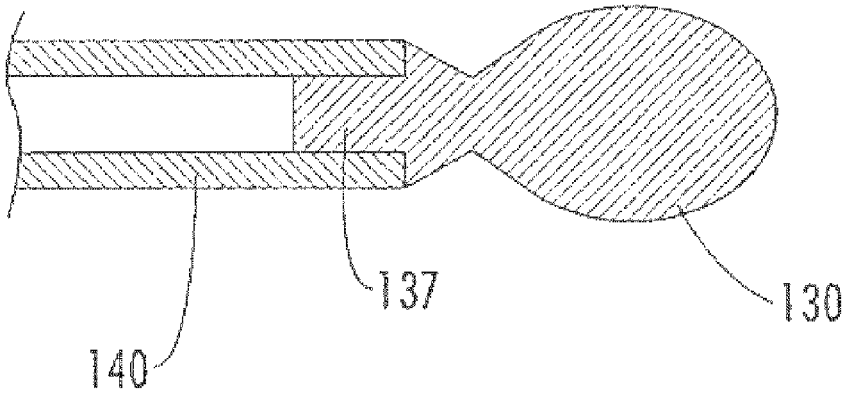

FIG. 4a is a schematic illustration of an inner shaft 140 of a surgical instrument 100 according to an embodiment of the invention with a burr bit 130 provided at its distal end. FIG. 4b is a cross-sectional schematic illustration of an inner shaft 140 and a burr bit 130 showing an example of how they may be joined together. In this example, the burr bit 130 has a base portion 137 that is inserted into the inner shaft and secured. The base portion 137 and the inner shaft 140 may be secured together by any appropriate methods such as press fitting, welding, ultrasonic welding. Alternatively the burr bit 130 may be secured to the inner shaft 140 using an adhesive. The burr bit 130 has helical cutting or abrading edges 131 on the head portion and a base portion 137 for attaching the burr bit 130 to the inner shaft 140. The inner shaft 140 is shown as a hollow tube in this example, but it may also be a flexible solid shaft made from such elastic material as Nitinol metal alloy.

The soft tissue resector 300 discussed in reference to FIG. 3 may also utilize a similar inner shaft. In that embodiment, a soft tissue resector bit 330 would be disposed at the distal end of the inner shaft. And to enable the vacuum tissue removal feature of the soft tissue resector 300, the inner shaft in this embodiment would have a tubular structure (as the inner shaft illustrated in FIG. 4b) with one or more channels therein. The soft tissue resector bit 330 may be provided with one or more channels or pathways through its base portion so that the open spaces 335 between the tissue cutting teeth 333 of the tissue resector bit 330 are communicatively connected to the one or more channels of the inner shaft. A vacuum drawn through the inner shaft of the instrument can then remove soft tissue debris from the surgical site using the open spaces 335 between the tissue cutting teeth 333 as the intake openings.

Figure 5A:
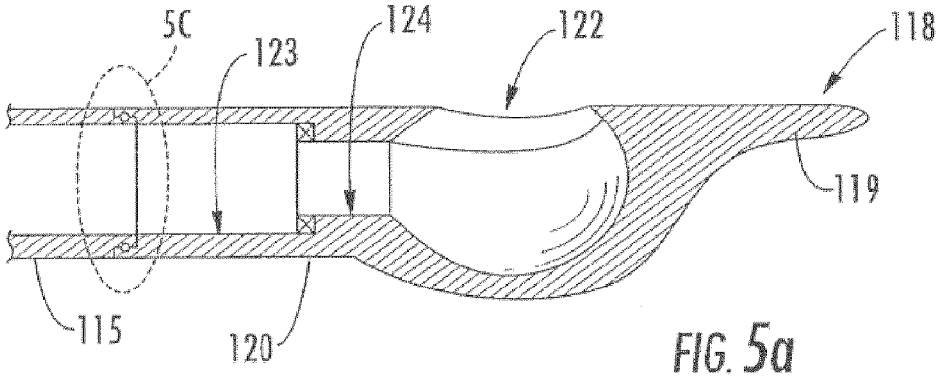
FIG. 5a is a cross-sectional schematic illustration of a protective hood of the surgical instrument of FIG. 1.
Figure 5B:
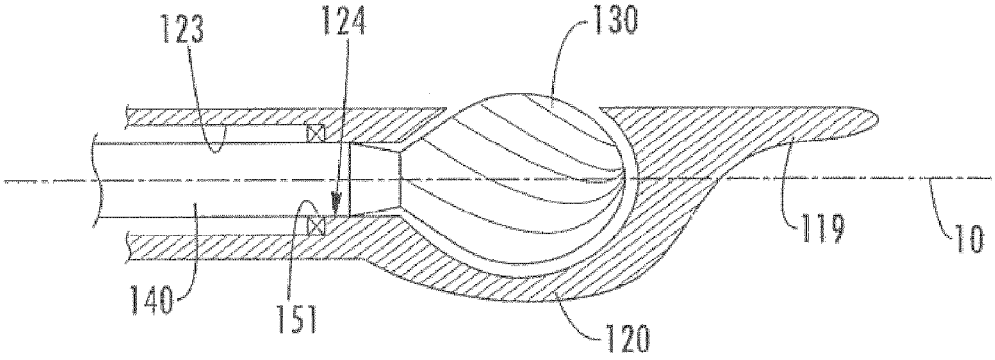
FIG. 5b is a cross-sectional schematic illustration of the protective hood of FIG. 5a with the inner shaft member of FIG. 4a disposed therein.
Figure 5C:
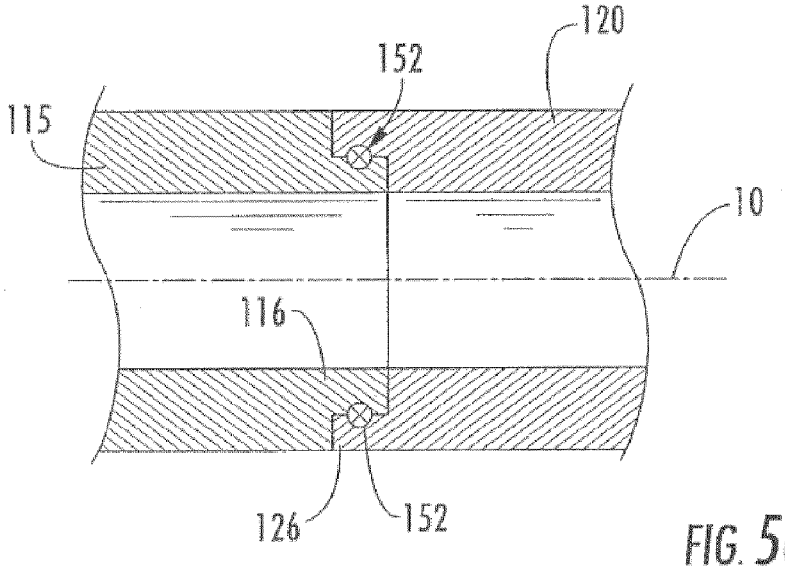

Referring to FIGS. 5a-5c, exemplary detailed views of the rotatable protective hood 120 and the burr bit 130 assembly will be discussed. FIG. 5a is a cross-sectional schematic illustration of the outer tube 115 and the rotating protective hood 120 of the surgical instrument 100 of FIG. 1. The rotating protective hood 120 is rotatably attached to the distal end of the outer tube 115. The distal end of the protective hood is the dissecting foot plate 119. The protective hood 120 has an open space 121 in which the burr bit 130 (or a soft tissue resector bit 330 in the dissecting soft tissue resector embodiment 300) attached to the inner shaft 140 may be disposed.

FIG. 5b is a schematic illustration of the protective hood 120 of FIG. 5a with the inner shaft 140 and the burr bit 130 disposed therein occupying the open space 121 inside the protective hood 120. The inner shaft 140 is disposed inside the protective hood 120 and the outer tube 115 in such manner so that the inner shaft 140 can rotate about the longitudinal axis 10. The inner surface of the outer tube 115 comprises a first inner cylindrical side wall 123 having a first diameter and a second inner cylindrical side wall 124 having a second diameter that is smaller than the first diameter. This second inner cylindrical side wall surface 124 provides a bearing means 151 that comes in contact with the inner shaft 140 allowing the inner shaft 140 to rotate about the longitudinal axis 10 with low friction. A portion of the burr bit 130 is shown exposed by the opening 122 in the protective hood 120.

FIG. 5c is a detailed schematic illustration of region B in FIG. 5a. This illustration is one example of the rotational engagement between the protective hood 120 and the outer tube 115. The proximal end of the protective hood 120 may form an outer sleeve 126 and the distal end of the outer tube may form an inner sleeve 116 that mate with one another and a suitable bearing means 152 is disposed between the mating sleeve surfaces to allow the protective hood to rotate about the longitudinal axis 10 of the distal end of the instrument. The rotatable joint between the outer tube 115 and the protective hood 120 may be formed in a variety of other configurations that are well known in the art.

The power drive mechanism for rotating the inner shaft/burr bit assembly may be any one of the known mechanisms known in the art. Many examples can be found in many conventional high speed surgical burrs, abraders, and other hand held power surgical instruments. Electrical motors or pneumatic power driven driving mechanisms commonly found in such instruments may be used to power the instrument of the invention.

As illustrated in FIGS. 1a, 2a and 3a, the outer tube 115, 215, 315 of the instruments of the invention may preferably include an angled neck portion 117, 217, 317 whose angle may be variably controlled. The power drive mechanism utilized in those embodiments would have to accommodate the angled neck. Many known flexible coupling mechanisms may be utilized here to transmit the rotational motion of the power drive mechanism, usually housed in the hand piece 114, 214, 314, to the burr bit 130, 230 or the soft tissue resector bit 330. Such flexible coupling mechanism may be, for example, multiple hinged linkages used to drive socket wrenches or helical coil flexible connectors often used with hand held drills. In another embodiment, the flexible neck portion 117, 217, 317 of the instrument may be hollow structures and a solid shaft made of elastic materials such as Nitinol metal alloy provided therethrough may connect the power drive mechanism to the tool bits 130, 230, 330 for actually driving the tool bits. One example of a flexible coupling mechanism is disclosed in U.S. Pat. No. 5,411,514 (Fucci et al.), the disclosure of which is incorporated herein by reference.

Figure 6A:
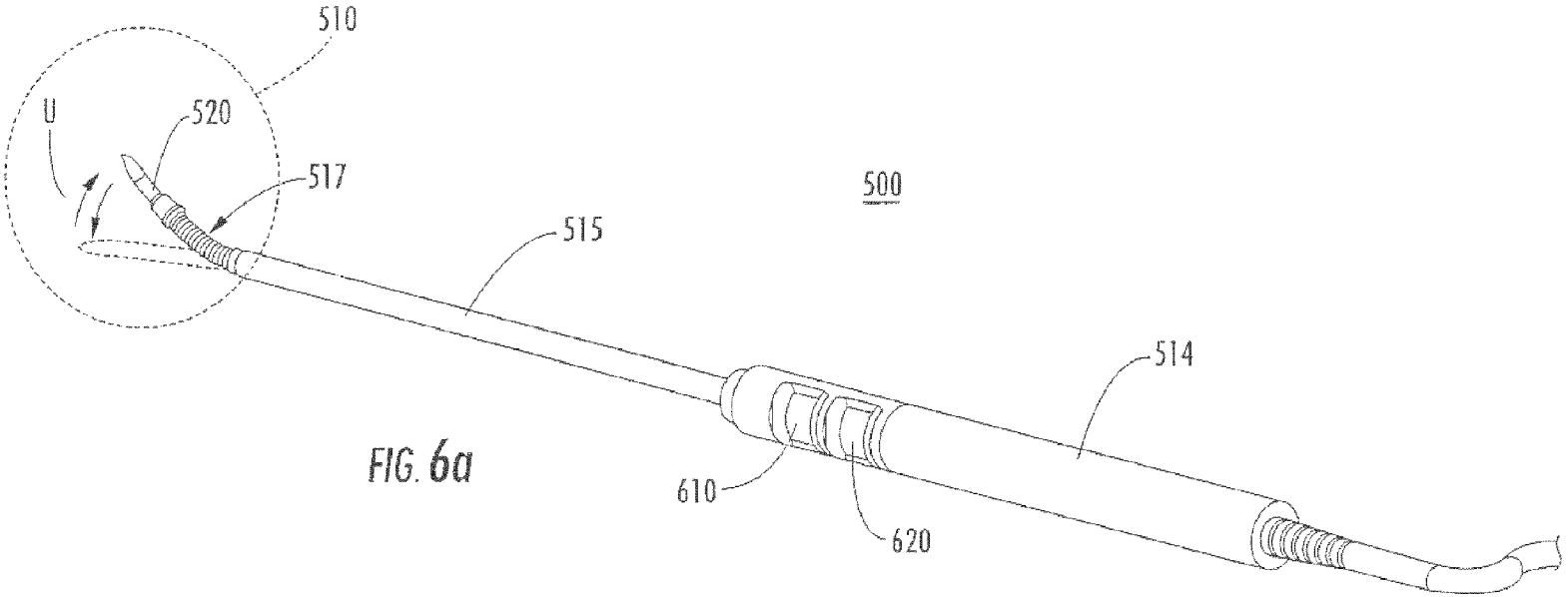
FIG. 6a is an isometric view of a surgical instrument according to an embodiment of the invention.
Figure 6B:
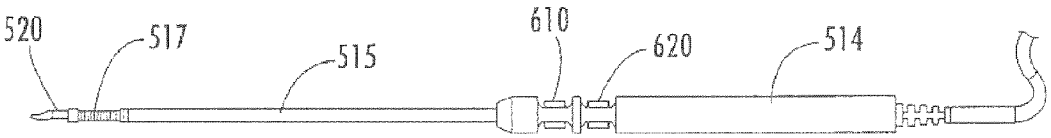

Referring to FIGS. 6a and 6b, a surgical instrument 500 according to another embodiment of the invention is disclosed. The surgical instrument 500 is well suited for the surgical operations discussed herein. The surgical instrument 500 has an elongated shape with a surgical instrument tool at the distal end 510 and a hand piece 514 at the proximal end. Connecting the hand piece 514 and the distal end 510 of the surgical instrument 500 is a shaft portion 515. The dimensions of the shaft portion 515 and the distal end 510 of the surgical instrument 500 are such that they can be inserted through a cannula to reach the surgical site percutaneously. Provided at the distal end 510 is a burr bit partially enclosed by a protective hood 520. The protective hood 520 and the burr bit are connected to the shaft portion 515 by a flexible neck portion 517. The flexible neck portion 517 is controllably bendable in one direction such as the dorsal direction marked by an arrow U in FIG. 6a. Although a configuration of the device 500 where the flexible neck portion 517 is configured to be controllably bendable in the dorsal direction U is shown, the device can be configured to be controllably bendable in any other direction (e.g. ventral direction) as desired. The hand piece 514 may be provided with thumb wheels 610 and 620, one for controlling the rotational position of the protective hood 520 and the latter for controlling the bending angle of the flexible neck portion 517. The hand piece 514 may house a power drive mechanism for driving the burr bit. Such power drive mechanism may be any suitable source that can rotate the burr bit at high speeds, such as an electric motor or a pneumatic drive mechanism.

Figure 7A:
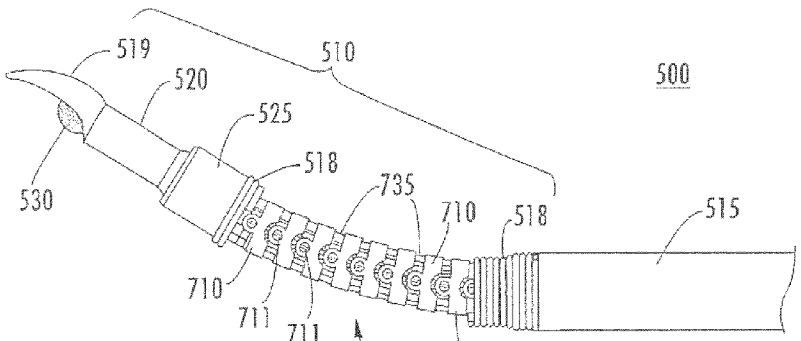
Figure 7B:
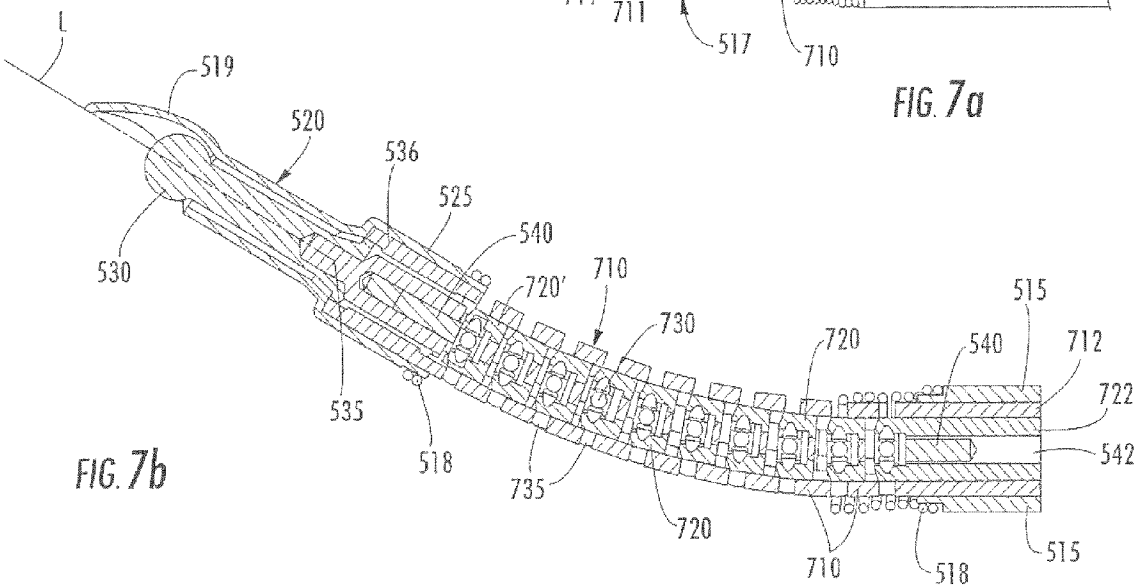

More detailed views of the distal end 510 of the surgical instrument 500 are illustrated in side elevational view FIG. 7a and a longitudinal sectional view FIG. 7b. The protective hood 520 includes a dissecting foot plate portion 519 which partially covers the burr bit 530 leaving the burr bit 530 partially exposed in one direction for removing bone material. The protective hood 520 is rotatable about the longitudinal axis L of the burr bit 530 (which is also the longitudinal axis of the surgical instrument 500. The protective hood 520 has a base portion 525 that is connected to the tubular shaft 515 via a flexible sleeve 518, which in turn is connected to the thumb wheel 610. The user can turn or rotate the protective hood 520 by turning the thumb wheel 610 to adjust the exposure direction or the angle of attack for the burr bit 530 as desired during a surgical procedure.

As illustrated in the sectional view of FIG. 7b, the connection between the base portion 525 of the protective hood 520 and the flexible sleeve 518 may be achieved by a friction fit. In FIGS. 7a and 7b, the flexible sleeve 518, which is a helical coil type in this exemplary embodiment, is only shown at the two ends so that the internal structures of the flexible neck 517 can be better illustrated. The proximal end of the flexible sleeve 518 is affixed to the tubular shaft 515. Again, this connection may be a friction fit connection.

Figure 8:
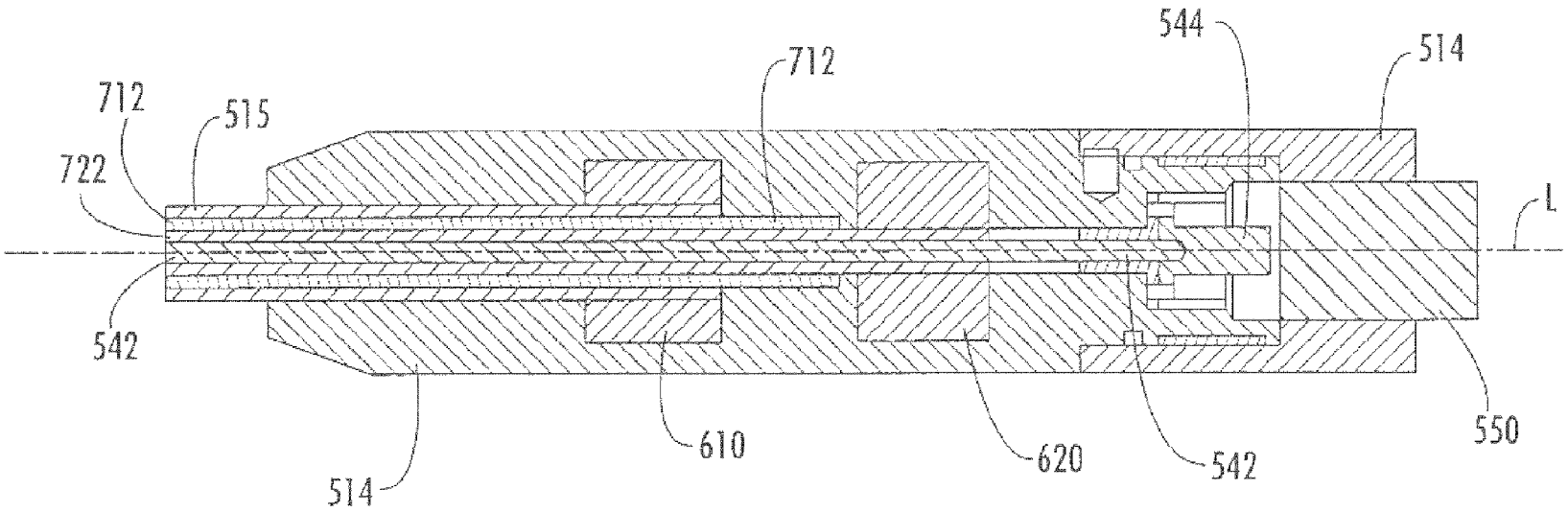

FIG. 8 is a sectional view of the hand piece 514 and the arrangement of the thumb wheels 610 and 620 is illustrated. The tubular shaft 515 is affixed to the first thumb wheel 610 so that turning the thumb wheel 610 also turns the tubular shaft 515 which, in turn, turns the flexible sleeve 518, which then turns the protective hood 520. The flexible sleeve 518 may be a helical coil type as illustrated in FIGS. 7a and 7b. The thumb wheel 610, the tubular shaft 515, the flexible sleeve 518, and the protective hood 520, all share a common rotational axis, which is the longitudinal axis L of the surgical instrument 500. The thumb wheel 610 may be provided with an appropriate mechanism (not shown) to lock the thumb wheel 610 from rotating in order to lock the orientation of the protective hood 520 after being adjusted. A variety of locking mechanism may be used for such purpose and it would be obvious to one of ordinary skill in the art to employ such mechanisms.

Nested inside the tubular shaft 515 is a first inner tube 712 (FIGS. 7b and 7c). The first inner tube 712 at the proximal end extends into the hand piece 514 and is friction fitted or affixed by other appropriate means to the hand piece 514 to prevent it from turning about the longitudinal axis L. At its distal end, the first inner tube 712 is connected to a series of outer links 710 which extend through the flexible sleeve 518 and hingeably connects to a tool-bit spindle housing 536 (FIG. 7b). As illustrated in FIG. 7a, the outer links 710 are hingeably linked to each other by a hinge 711. Because the first inner tube 712 is non-rotatably affixed to the hand piece 514, the outer links 710 also are not rotatable about the longitudinal axis L. The linkage formed by the outer links 710 are, however, bendable in one direction, the dorsal direction U, marked in FIG. 6a. This is because the outer links 710 are lined up so that the rotational axis M (FIG. 9a) through their hinges 711 are orthogonal to the dorsal direction U.

As illustrated in FIG. 7b, nested inside the first inner tube 712 is a second inner tube 722. The second inner tube 722 at its proximal end extends into the hand piece 514 and it is friction fitted or affixed by other appropriate means to the second thumb wheel 620. At its distal end, the second inner tube 722 is connected to a series of inner links 720 which extend through the outer links 710, with the last inner link 720' stopping at the end of the flexible neck portion 517. Thus, the inner links 720 are not connected to anything at the distal end. The inner links 720 are hingeably linked to each other by hinge pins 737 (FIG. 9b). As will be further discussed below in more detail, turning the second thumb wheel 620 rotates the inner links 720 and causes the assembly formed by the outer links 710 to bend up or down in the dorsal direction U.

As shown in FIG. 7b, nested inside the second inner tube 722 is a drive shaft 542. The drive shaft 542 may be a rigid shaft and at its proximal end it extends into the hand piece 514 and is affixed to a drive linkage 544 which connects the drive shaft 542 to a power drive unit 550. The power drive unit 550 may be an electric motor, a pneumatic drive unit, or any other suitable mechanism that can turn the drive shaft 542 at desired speeds. The drive shaft 542 at its distal end is affixed to a second drive shaft 540 that is flexible. The second drive shaft 540 may be made of strong and elastic material such as Nitinol alloy. The second drive shaft 540 extends through the inner links 710 and at the distal end is affixed to a tool-bit spindle 535. The tool-bit spindle 535 is, in turn, connected to a burr bit 530. Alternatively, the second drive shaft 540 may be directly connected to the burr bit 530 without the intermediate structure such as the spindle 535. Alternatively, the flexible second drive shaft 540 may extend all the way to the drive linkage 544 in the hand piece 514 so that a single piece drive shaft extends from the drive linkage 544 to the tool bit 530 or the tool-bit spindle 535. The tool-bit spindle 535 is journaled within the tool-bit spindle housing 536 so that the interface between the spindle 535 and the tool-bit spindle housing 536 is provided with a suitable lubricant or bearing arrangement so that the tool-bit spindle 535 may rotate with minimal frictional interference. Similarly, the interface between the tool-bit spindle housing 536 and the base portion 525 of the protective hood 520 is also provided with a suitable lubricant or bearing arrangement.

Figure 9D:
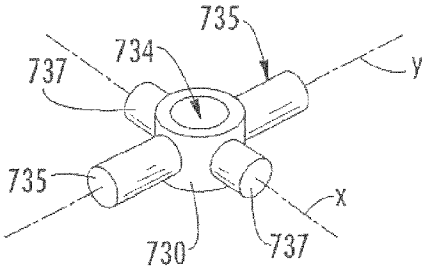
Figure 9C:
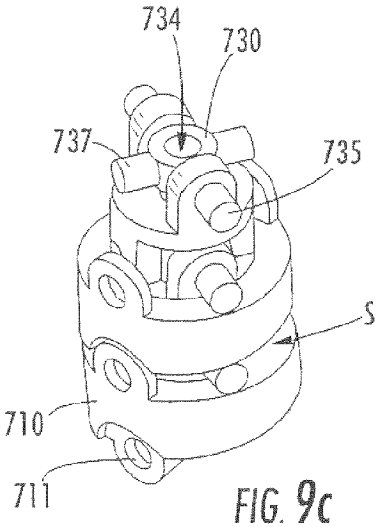
Figure 9B:
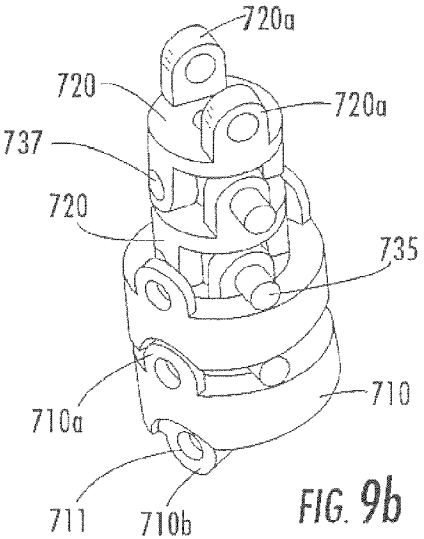
Figure 9A:
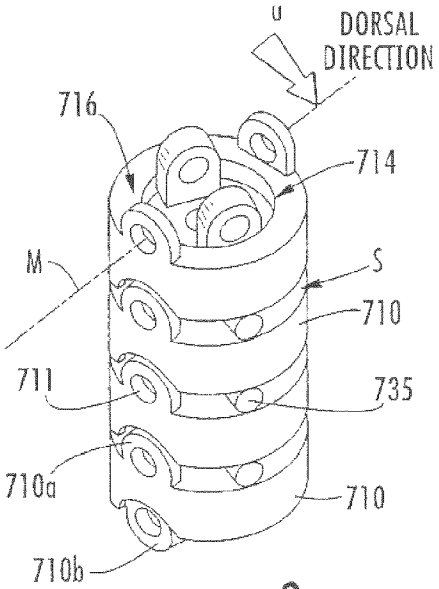
Figure 9F:
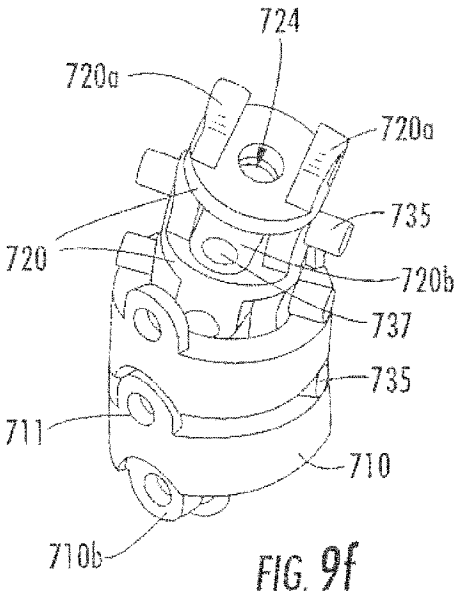

Referring to FIGS. 9a-9f and 10a-10c, the controllably bending mechanism of the flexible neck portion 517 achieved by the outer links 710 and the inner links 720 in this exemplary surgical instrument 500 will be described. As mentioned above, the outer links 710 form a non-rotating assembly that is bendable in one direction. The bending enabled by the hinges 711 connecting each outer links. Each of the outer links 710 have center hole 714 so that the outer links 710 form a bendable tube-like structure within which sits the structure formed by the inner links 720. The inner links are hingeably connected to each other by the hinge pins 737. Each of the inner links 720 also have center hole 724 (FIG. 9f). Each inner link 720 has a pair of lower ears 720b and a pair of upper ears 720a, transversely oriented from the lower ears 720b. The hingeable links between the inner links 720 are formed by a cross-shaped pin subassembly 730 (FIG. 9d). The pin subassembly 730 comprises a pair of short hinge pins 737. The hinge pins 737 mate with the lower ears 720b of the inner links 720 thereby hingeably connecting them. The pin subassembly 730 also comprises a pair of long camming pins 735 whose longitudinal axis Y is oriented transverse to the longitudinal axis X of the short hinge pins 737. The pin subassembly 730 is assembled in between two inner links 720 so that the camming pins 735 extend through the upper ears 720a of the inner links 720 and into camming spaces S formed between the outer links 710. The pin subassembly 730 is provided with center hole 734 that aligns with the center hole 724 of the inner links 724

Figure 9E:
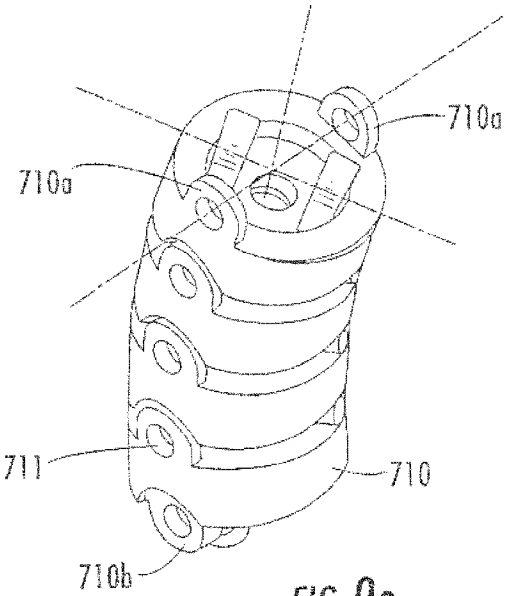
Figure 10A:
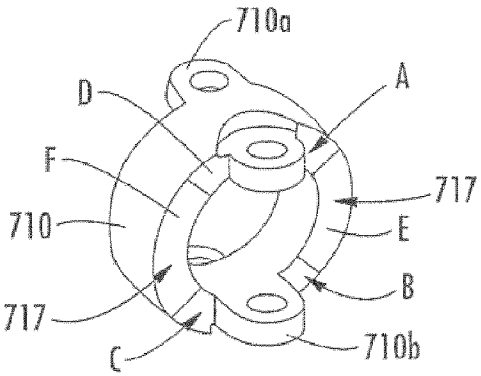
FIGS. 10a-10c are detailed illustrations relating to how the flexible neck portion bends.
Figure 10C:
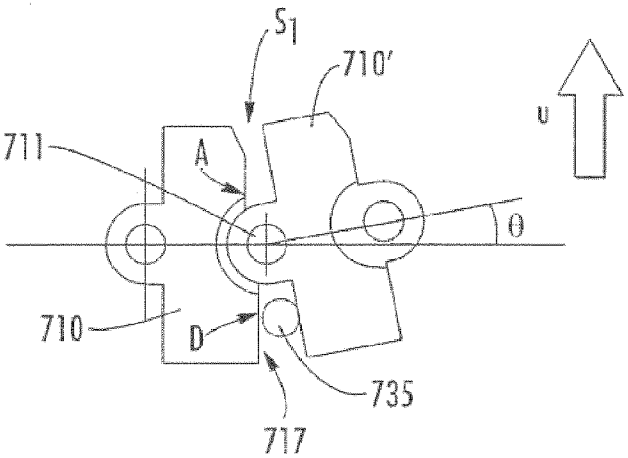
Figure 10B:
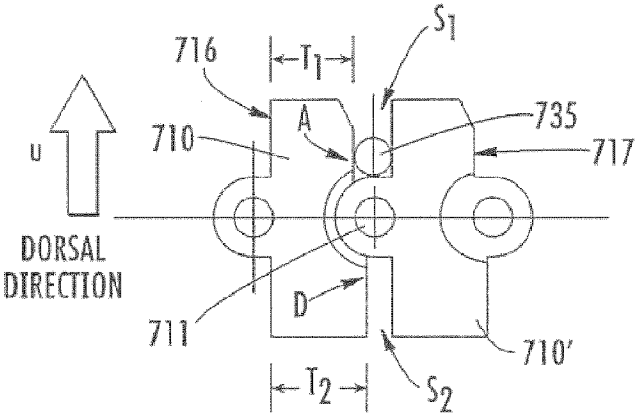

Referring to FIG. 10a, each outer link 710 has a first surface 716 that is flat and a second surface 717 that is specifically contoured. The second surface 717 forms the camming surface for the camming pins 735 which extends into the camming space S formed between the outer links 710. The camming surface 717 is contoured so that as the camming pins 735 rotates in the camming space S, the two adjacent outer links 710 are forced to bend about the hinge 711 in the dorsal direction U and back to the straight configuration. The camming surface 717 of the outer link 710 is contoured to have at least six regions marked as A, B, C, D, E, and F in FIG. 10a. FIG. 10b illustrates the configuration where two adjacent outer links 710 and 710' are in a straight arrangement. Thus, this represents the configuration where the flexible neck 517 of the surgical instrument 500 is, in turn, straight. The inner links 720 have been rotated so that one end of their camming pin 735 is positioned in the camming space S. The camming pin 735 is at the region A of the camming surface 717. The opposite end (not shown) of the camming pin 735 is on the opposite side at the region C of the camming surface 717. This position of the camming pin 735 will be referred to as the A-C position. Illustrated in FIG. 10c is the configuration in which the outer links 710 and 710' are at their maximum bending angle θ. The camming pin 735 is now at the regions D and B of the camming surface 717. This position of the camming pin 735 will be referred to as the B-D position. As illustrated in FIGS. 10b and 10c, the thickness T1 of the outer link 710 at camming region A is thinner than the thickness T2 of the outer link 710 at the camming region D. Correspondingly, the camming space S1 is larger than the camming space S2. Thus, as the camming pin 735 transitions from the A-C position to the B-D position, the camming pin 735 pushes the outer links 710 and 710' apart at the S2 side and causing the outer links to pivot relative to each other about the hinge 711. By rotating the inner links 720 and moving the camming pin 735 back to the A-C position, the camming pin 735 now pushes the outer links 710 and 710' apart at the S1 side pivoting the outer links back to the straight configuration shown in FIG. 10b. FIG. 9a illustrates the outer link assembly in a position where the camming pins 735 are somewhat close to the A-C position and FIG. 9e illustrates the outer link assembly in a position where the camming pins 735 are somewhat closer to the B-D position. It should be noted that the maximum range for the amount of bending that may be manipulated for a given surgical instrument 500 can be varied as desired by changing the contour of the camming surface 717 of the outer links and the number of outer links used to form the flexible neck portion 517.

Figure 11A:
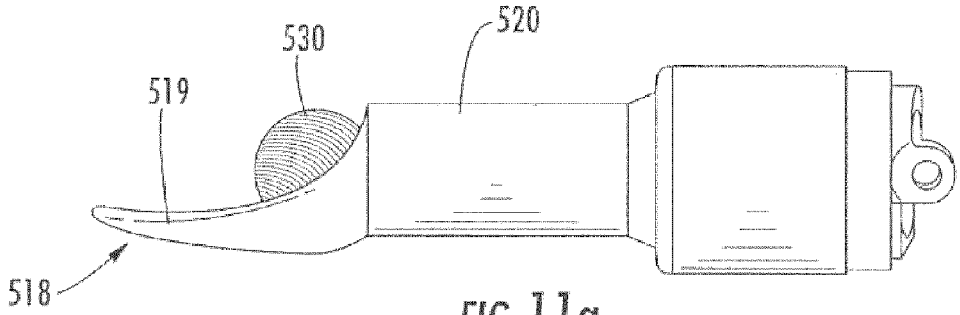
FIGS. 11a-11d are detailed illustrations of a burr hood according to an embodiment of the invention.
Figure 11B:
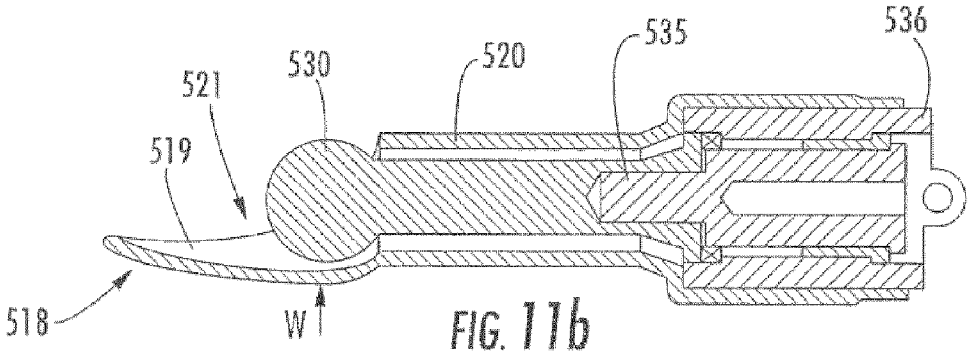
Figure 11C:
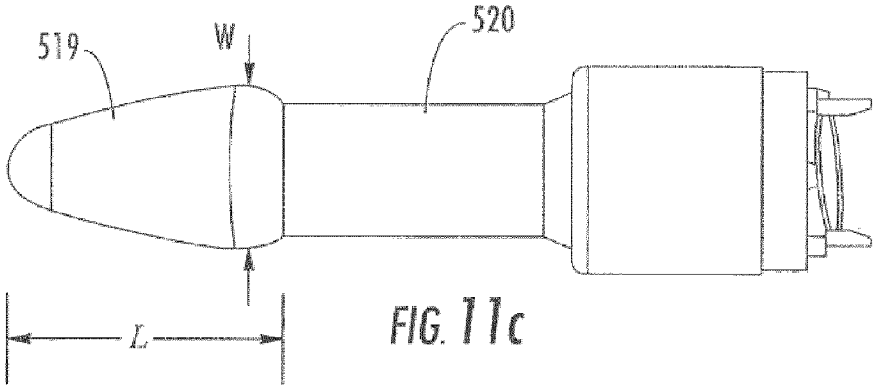
Figure 11D:
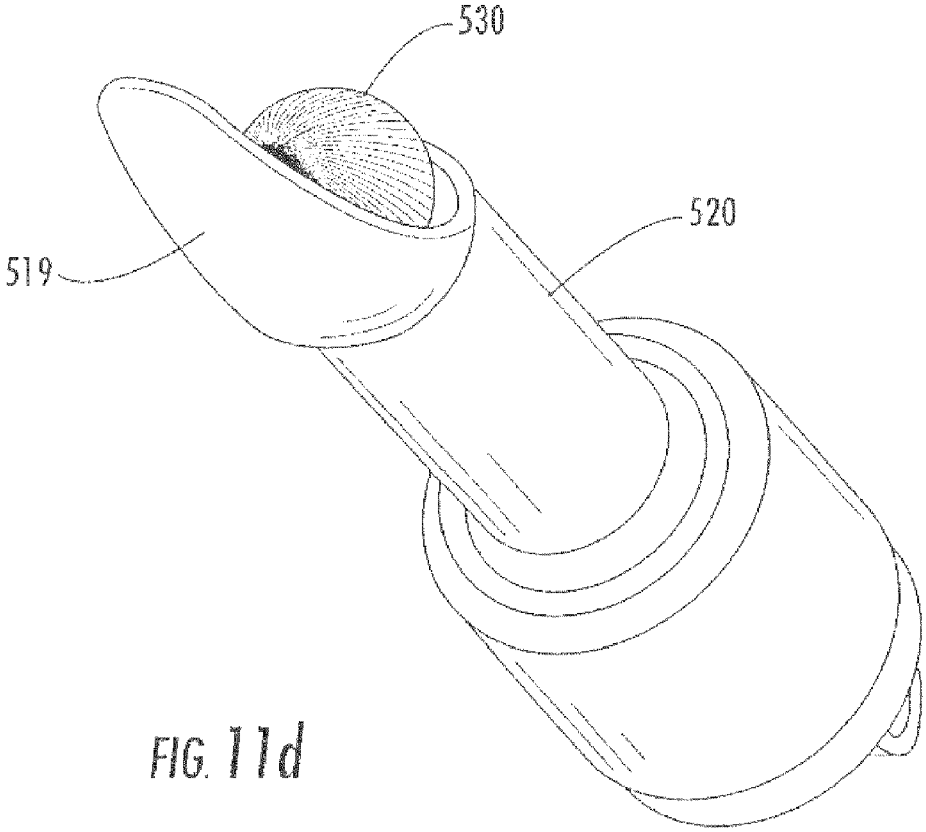

FIGS. 11a-11d are more detailed illustrations of the protective hood 520 of the surgical instrument 500 of FIG. 6a. The side view, FIG. 11a, and the sectional view FIG. 11b, show that the dissecting foot plate portion 519 of the protective hood 520 partially enclose the burr bit 530. The dissecting foot plate portion 519 in this exemplary embodiment is similarly shaped to the Woodson dissecting tool, with the dissecting foot plate 519 extending from the widest portion W of the protective hood 520 towards the distal tip 518 beyond the burr bit 530 providing a space 521. The burr bit end of the surgical instrument 500 can be inserted into a surgical site, such as the interval between the nerve root and the encroaching bone in a neural foramen without the need for a separate dissecting tool and without the risk of damaging the surrounding soft tissue such as the nerve root. The surgeon would rotate the protective hood 520 so that the foot plate portion 519 is positioned to be between the burr bit 530 and the nerve root as the surgeon inserts the burr bit end of the instrument into the surgical site.

Figure 12A:
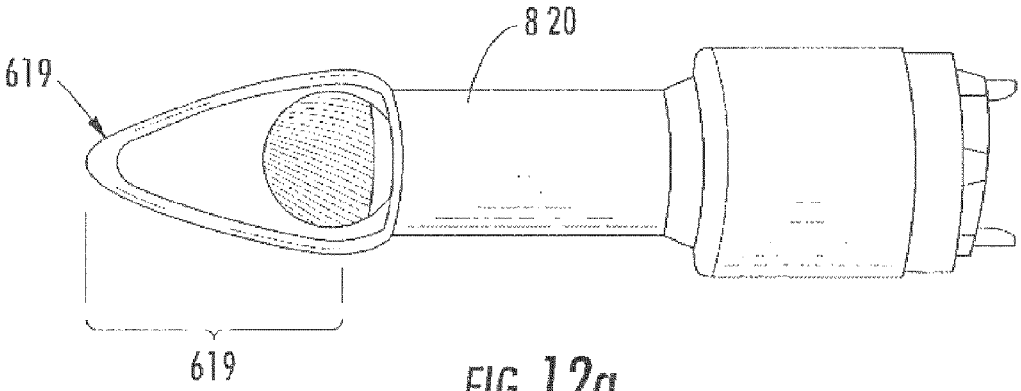
FIGS. 12a-12c and 13a-13c are detailed illustrations of a burr hood according to another embodiment of the invention.
Figure 12B:
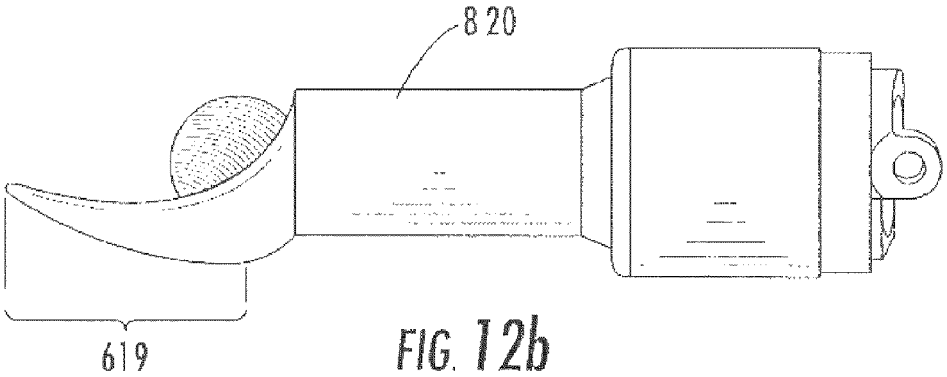
Figure 12C:
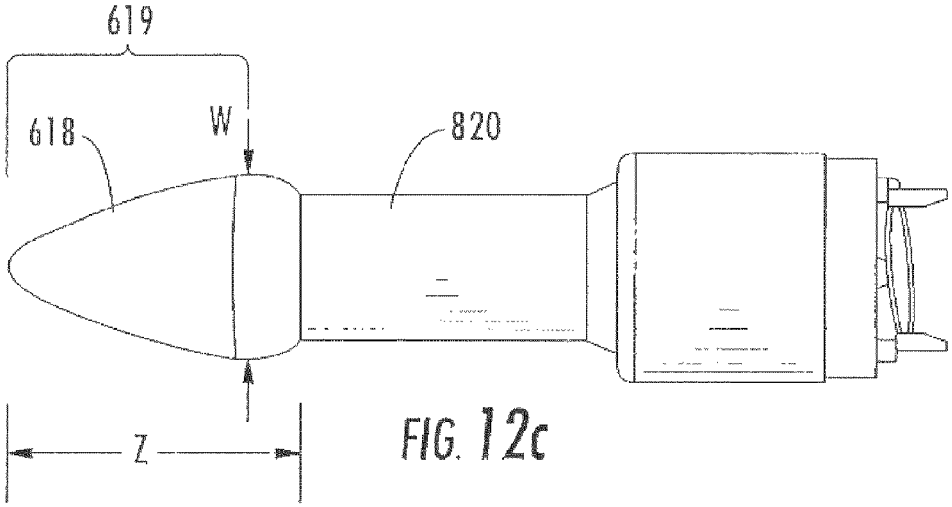

FIGS. 12a-12c are illustrations of another protective hood 820 for the surgical instrument 500 having another dissecting foot plate 619 having a pointed or tapered distal tip 618 according to another embodiment. As mentioned above, the dissecting foot plate portion may be configured and adapted to have many different shapes that are appropriate for a particular application but all for providing a dissecting function.

Figure 13A:
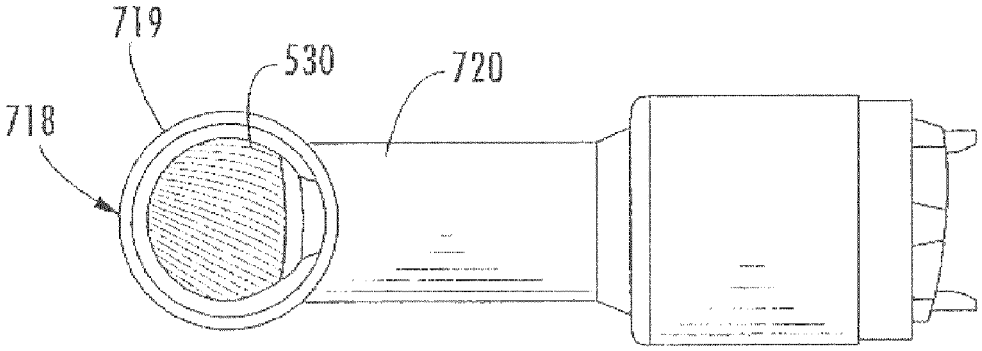
Figure 13B:
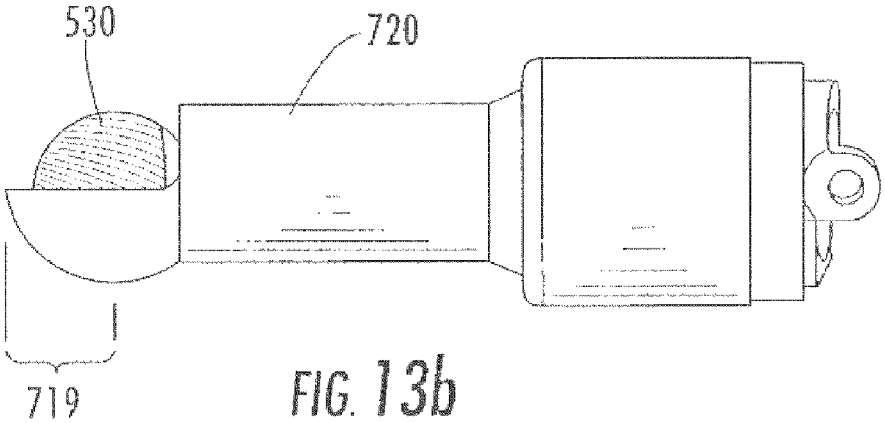
Figure 13C:
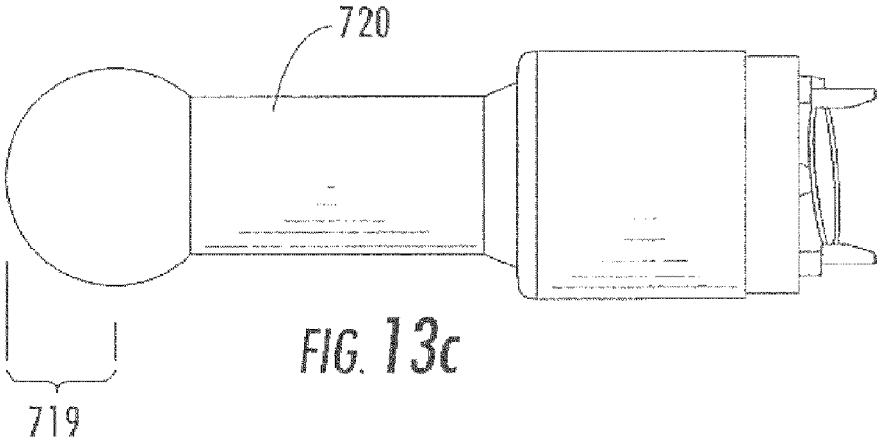

FIGS. 13a-13c are illustrations of another protective hood 720 for the surgical instrument 500 having a curette-type dissecting foot plate 719 according to another embodiment. The curette-type dissecting foot plate 719 of this embodiment does not extend out beyond the burr bit 530 as much as the Woodson-type dissecting foot plates 519, 619. The curette-type dissecting foot plate 719 has a short curved shape.

The dissecting foot plate portion s 519, 619 and 719 have length Z of about 7.5 mm and a diameter at the widest portion W of about 4.5 mm. For surgical applications involving lumbar decompression surgical procedures such as lumbar laminectomy and foraminotomy, the dissecting foot plate portion may have a length of about 1 mm (currette-like tip) to about 8 mm (Woodson-like tip). The diameter of the foot plate portion at the widest portion W may be about 2 mm to 10 mm depending on the burr bit size.

With current minimally invasive lumbar decompression techniques, a retracting cannula is placed at the interspace percutaneously via sequential dilators. This technique works well for disc herniations where the pathology can be accessed at the interspace. The draw back to this technique with lumbar decompressions is that the ipsilateral lateral recess and foramen are extremely difficult to decompress because the line of sight afforded by the cannula does not allow the surgeon to get a direct view into the recess or the foramen on the ipsilateral side. Therefore, some surgeons have modified the technique and taken the cannula and directed it contralaterally to afford a view at the contralateral lateral recess and foramen. The drawback of this technique is that you disrupt the interspinous ligament and reaching across the dural space risks tearing the dura. In addition, attempting a foraminal decompression and lateral recess decompression in this fashion is technically extremely demanding because of the limited view and the limited maneuverability afforded by the small working diameter of the cannula. The cannulas typically have a diameter of about 2 centimeters. This could be made even more technically demanding in a patient with an extremely stenotic lateral recess and foramen.

The spinal instruments of the invention provides many advantages over the conventional instruments in performing minimally invasive lumbar decompressions. Lateral recess decompression can be performed on the ipsilateral side and also a foraminotomy can be performed on the ipsilateral side. Therefore, the interspinal ligaments can be preserved and all that is necessary to complete a full decompression is making a midline incision to bring the cannula to one side of the spinous process and the interspinous ligaments to perform one side of the lateral decompression. The cannula is then pulled out and reenter the spine on the contralateral side, through the same incision, on the other side of the spinous process and interspinous ligament and perform the contralateral lumbar lateral recess and foraminal decompression. In this way the interspinous ligament and the spinous processes are preserved and that posterior tension band is not violated. In order to perform the lateral recess decompression, an endoscope must be placed, similar to the conventional scopes that can be attached to the retracting cannula, however, it needs to be angled at a 60-70 degree angle so that it has a view directly into the lateral recess and the foramen.

Because the surgical instruments 100, 200 of the invention do not require a large amount of force or a large arc of motion to perform a bone resection, the lateral recess and foraminal decompression can be performed safely and accurately in minimally invasive setting. Because of the precision of bone resection allowed by the surgical instruments 100, 200 of the invention, the actual amount of bone that is resected can be minimized just to the bone that is encroaching on to the nerve root or the dural elements in the lateral recess. Thus, the amount of bony resection can be minimized to what is necessary to adequately decompress the neural elements. This maximally preserves the facet joints, thereby minimizing post-decompression instability.

A number of benefits are realized by the use of the surgical instruments of the invention described herein. For example, by performing the bone and ligament sparing lumbar decompression, the lamina can be preserved. The ligamentum just needs to be removed at the interspace, which often is the main source of compression, and the bone encroaching the lateral recess from facet hypertrophy and the foraminal stenosis can be adequately decompressed using the dissecting burr embodiment and the soft tissue resector embodiment of the surgical instrument disclosed herein.

Since the amount of facet resection can be minimized and the posterior spinal ligaments preserved by using the surgical instrument of the invention, it may be possible to clinically avoid fusion in patients with mild instability and mild spondylolisthesis because most of the spinal stability and the spinal integrity can be preserved. However, in patients where fusions are deemed to be warranted, the decompressions can be performed in a minimally invasive setting and since the lamina are preserved, one can attempt an interlaminar spinal fusion. Also, because the intertransverse plane is not dissected, there is no lateral soft tissue stripping that needs to be performed lateral to the facets and the intertransverse plane, therefore the morbidity to the patient is significantly minimized and the patient's postoperative recovery will be enhanced. Thus, there is no additional soft tissue dissection that is required than is done with a normal laminectomy.

By using the surgical instruments of the invention, preservation of bone and interspinal ligaments can be maximized during spinal decompression procedures. And since a good portion of the spinal stability is maintained by preserving the bone and interspinal ligaments, the overall patient satisfaction will be much improved in the strictly lumbar decompression patients. Furthermore, by combining the decompression performed with the instruments of the invention with a minimally invasive interlaminar fusion, possibly supplemented with minimally invasive pedicle screw system, the spinal segment fusion can be performed with a higher union rate and faster recovery times since the intertransverse muscle plane can be spared.

The surgical instruments of the invention also have applications in other areas of the spine. In the cervical spine, for example, the surgical instrument may be used for posterior foraminotomies. In such procedure, the dorsal surface of the spinal nerve root is first located and the surgical instrument is inserted overlying the nerve root under microscopic visualization and a foraminotomy may be performed that maximally preserves the cervical facet joint.

The dissecting burr embodiment of the disclosed surgical instrument can also enhance anterior cervical surgery, for example, during anterior cervical corpectomies. The width of the corpectomy trough is limited by concerns of the vertebral artery being violated at the lateral margin. Often the lateral decompression is incomplete because of fear of violating the vertebral artery, which can be catastrophic. With the use of the surgical instrument of the present disclosure, the dissecting portion of the burr can be inserted into the interval between the vertebral artery and the lateral margins of the anterior cervical vertebral body and resect the lateral bony edge. This would allow the surgeon to perform a complete cervical corpectomy rather than a partial one.

Also, for anterior cervical disc work, the dissecting burr embodiment of the surgical instrument can be used to perform anterior cervical foraminotomies and osteophytectomies by inserting the burr into the interval between the lateral margin of the uncus and the vertebral artery by protecting the vertebral artery and allowing complete resection of the uncovertebral joint and thereby decompressing the foramina laterally and allowing preservation of the disc space medially and avoiding cervical fusion.

According to an aspect of the invention, the various embodiments of the instruments described herein may be configured so that irrigation fluid may be delivered to the surgical site via the instrument. There are many examples of surgical instruments known in the art having such irrigating feature that may be incorporated into the instruments of the invention. Example of burring or similar type of instruments with irrigation feature are described in, for example, U.S. Pat. Nos. 5,782,795 (Bays); 6,068,641 (Varsseveld); and 6,503,263 (Adams), the disclosures of which are incorporated herein by reference. In both the dissecting burr and the dissecting soft tissue resector embodiments of the surgical instrument, channels or pathways may be provided within the instrument for supplying irrigation fluid to the surgical site. Irrigation fluid would serve to assist in removal of tissue debris from the surgical site as well as cooling the surgical tool tip, the burr bits 130, 230 and the soft tissue resector bit 330, during the surgical procedure. Keeping the tool tip cool prevents damaging bone, nerve, or surrounding tissues during the surgical procedure. The irrigation can also help to collect the bone or other tissue debris for removal from the surgical site.

The instruments of the invention may also be configured for removing the tissue debris from the surgical site by vacuum. As discussed in reference to the soft tissue resector embodiment of the invention, the surgical tool tip may be configured to have open spaces between the cutting or abrading teeth sufficiently large for removal of tissue debris. The protective hood 120, 220, 320 or the outer tube 115, 215, 315 may also be configured with openings that may serve as intake ports for removing tissue debris by suction from in and around the surgical site. Additional detailed description of the soft tissue resector embodiment is described below in connection with FIGS. 27a, 27b. Many examples of surgical burrs and other abraders having such tissue removal features are known in the industry.

Figure 14A:
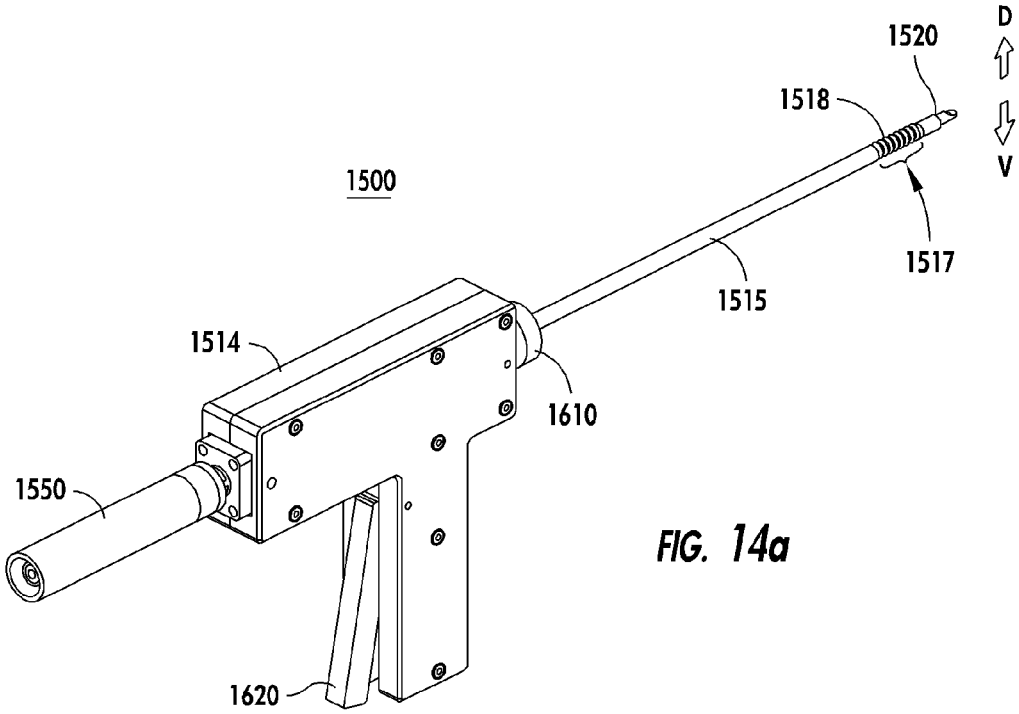
FIGS. 14a-14b are isometric views of a high speed burr surgical instrument 1500 according to another embodiment.
Figure 14B:
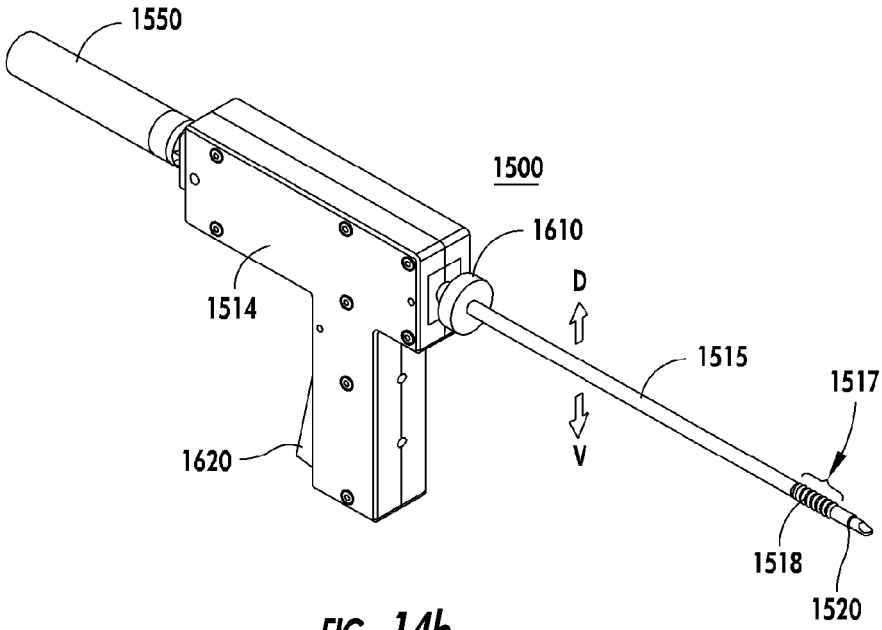

FIGS. 14a and 14b show isometric views of a surgical instrument 1500 according to another embodiment of the present disclosure. The surgical instrument 1500 comprises a hand piece 1514 that includes a tool bit power drive unit 1550, a first control member 1610 and a second control member 1620. The surgical instrument 1500 also includes a shaft portion 1515 that is connected to the hand piece 1514 at its proximal end and connected to a protective hood 1520 at its distal end. As shown in FIG. 14a, the top side of the surgical instrument 1500 and its shaft portion 1515 is identified as the dorsal side D and the bottom side is identified as the ventral side V.

A flexible neck portion 1517 connecting the protective hood 1520 to the distal end of the shaft portion 1515 is configured to be controllably bendable from the hand piece 1514. The flexible neck portion 1517 is preferentially bendable in one direction, such as towards the dorsal side D or towards the ventral side V of the shaft portion 1515, or in any other desired direction. The surgical instrument 1500 is configured to control the bending of the flexible neck portion 1517 by manipulation of the second control member 1620.

The first control member 1610 is operably connected to the protective hood 1520 for controlling the rotation of the protective hood 1520 relative to the hand piece 1514 and the drive shaft 1542. The first control member 1610 is connected to the proximal end of the shaft portion 1515 which is, in turn, connected to the protective hood 1520 via the flexible neck portion 1517. Rotating the first control member 1610 controls the rotation of the protective hood 1520 relative to the hand piece 1514 and the drive shaft 1542.

Figure 15:
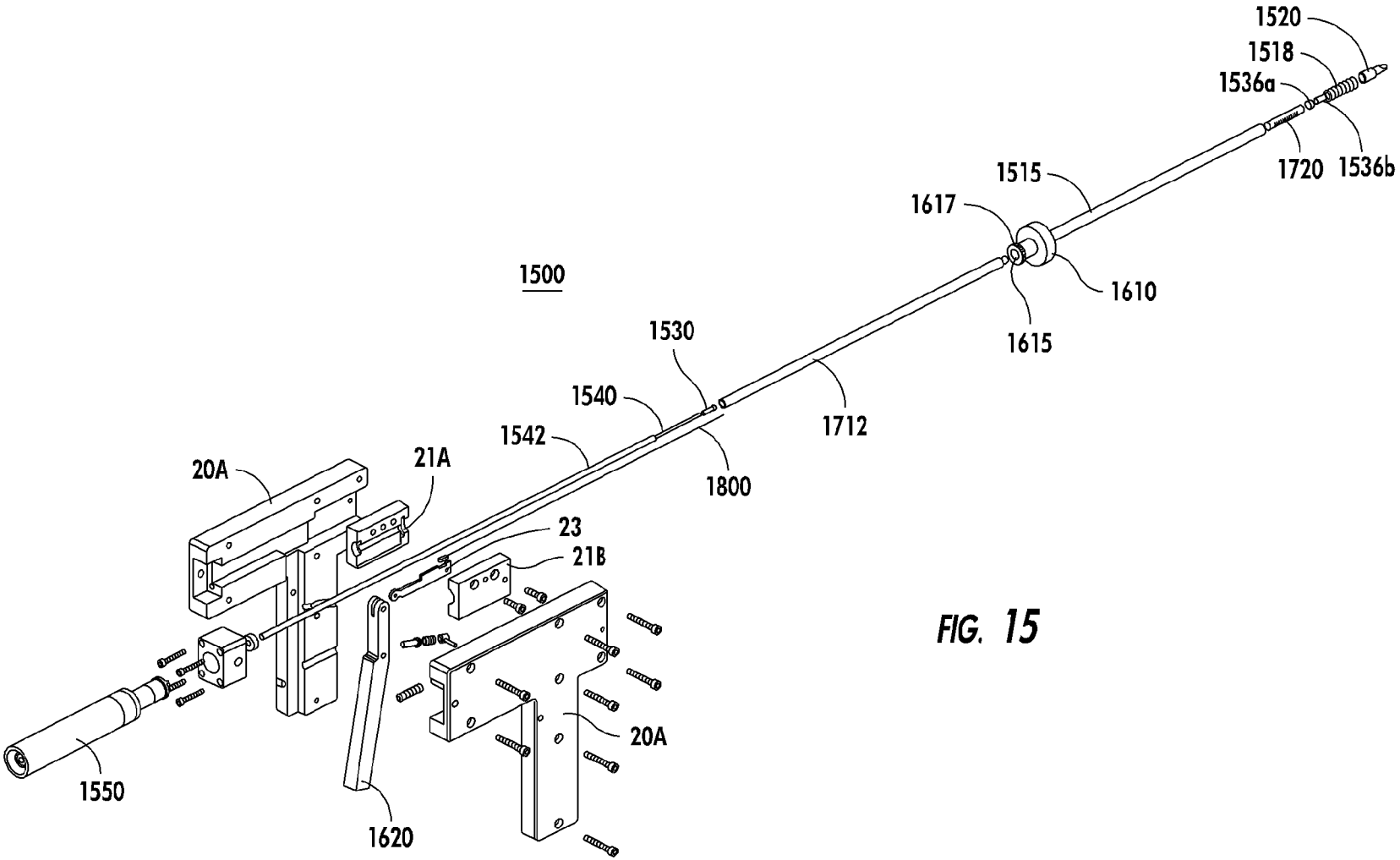
FIG. 15 is an exploded view of the high speed burr surgical instrument 1500.
Figure 27A:
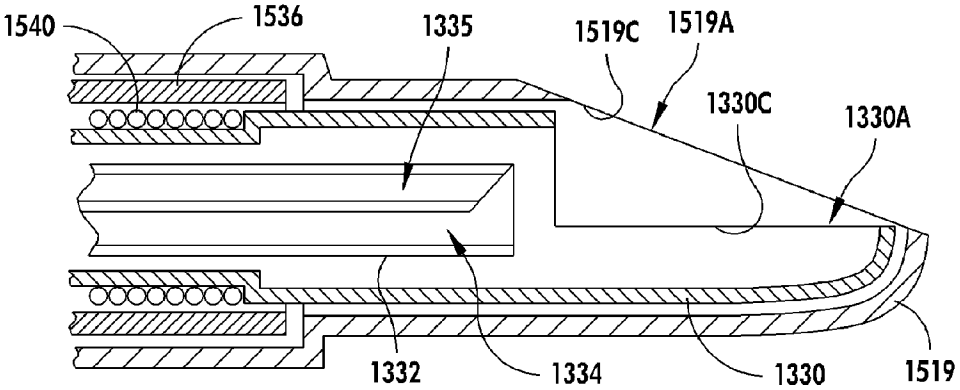
FIGS. 27a and 27b are longitudinal cross-section view and a plan view, respectively, of the distal end of the surgical instrument 1500 provided with a soft tissue resector bit according to another embodiment.
Figure 27B:
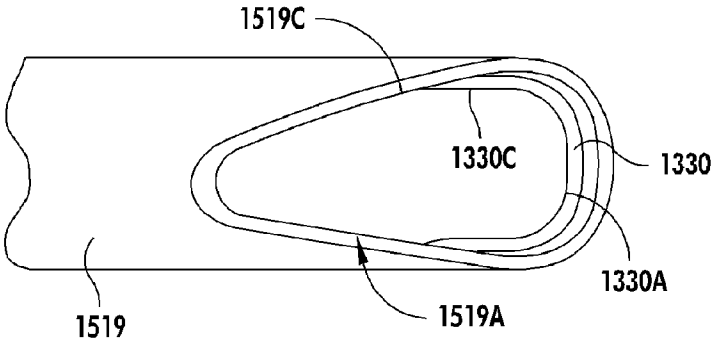

FIG. 15 is an exploded view of the surgical instrument 1500. The main part of the hand piece 1514 comprises two halves 20A and 20B. An inner shaft 1712 extends through the shaft portion 1515 and a drive shaft 1542, in turn, extends through the inner shaft 1712. The drive shaft 1542 connects the power drive unit 1550 to the surgical tool bit 1530. As discussed above in connection with other embodiments the surgical tool bit 1530 can be a burr bit for removing bone material or a soft tissue resector bit. A detailed view of a surgical instrument 1500 configured and adapted for soft tissue resection using a soft tissue resector bit is shown in FIGS. 27a and 27b and discussed below.

The surgical tool bit 1530 is connected to the distal end of the drive shaft 1542 via a flexible portion 1540. The flexible portion 1540 is configured with a structure that allows transmission of the torque from the drive shaft 1542 to the surgical tool bit 1530 while being able to bend. An example of the flexible portion 1540 is a coil shaft. The drive shaft 1542 is disposed in and extends through the inner shaft 1712 and rotates within the shaft 1712 when rotatably driven by the power drive unit 1550.

The inner shaft 1712 does not rotate and is affixed to the hand piece 1514 by being captured within the two halves 21A and 21B of a bearing block. The shaft portion 1515 is connected at the proximal end to the first control member 1610 and connected at its distal end to a flexible outer sleeve 1518 which is in turn connected to the protective hood 1520.

Figure 16A:
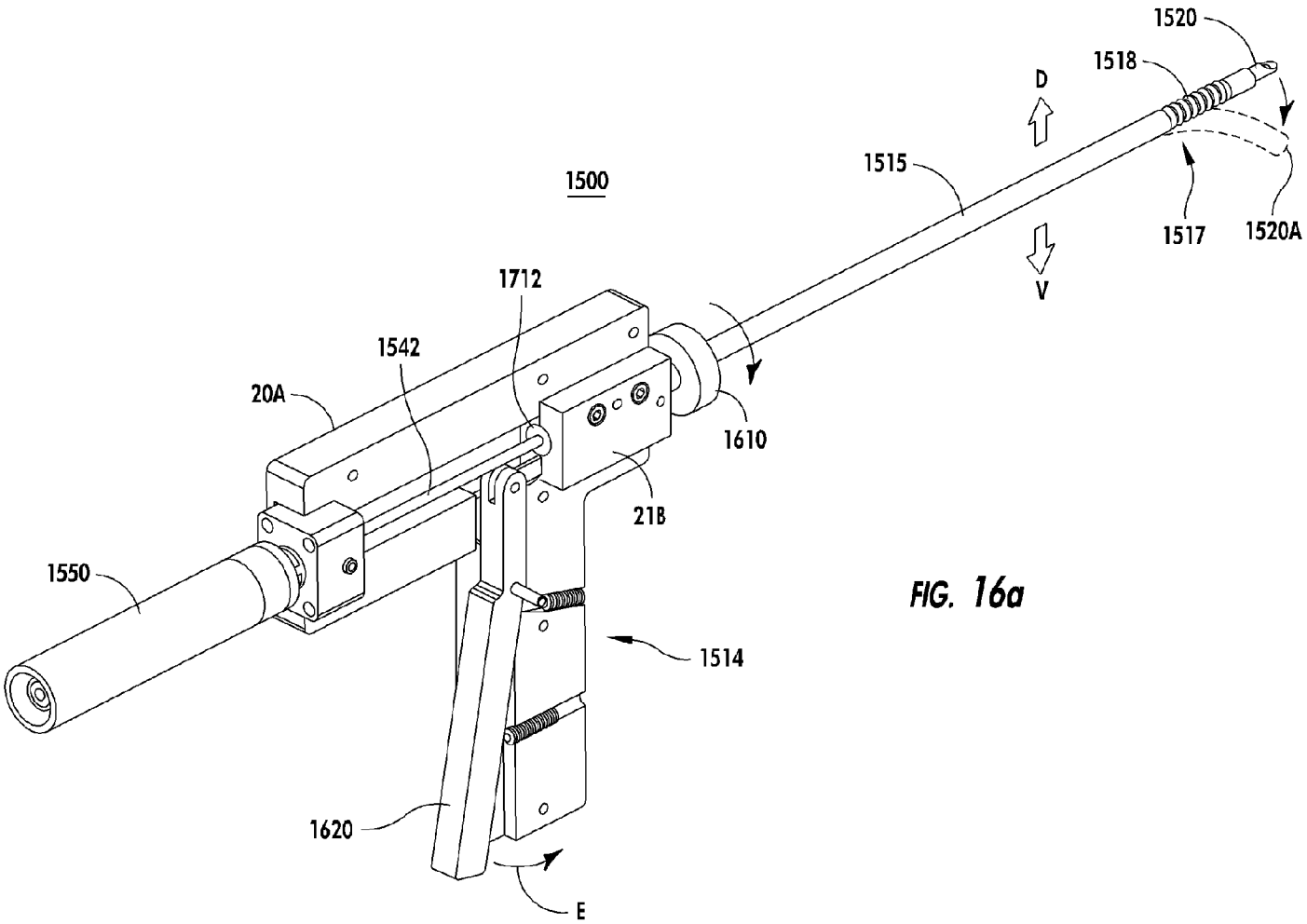
FIGS. 16a-16b are partial assembly views of the high speed burr surgical instrument 1500.

FIG. 16a is a partially assembled view of the surgical instrument 1500 showing the arrangement of the components of the surgical instrument 1500 within the hand piece 1514. In this view, one of the two halves 20B of the hand piece 1514 has been removed to show the internal arrangement. The drive shaft 1542 is in assembled position connected to the power drive unit 1550 and extending through the inner shaft 1712. The shaft portion 1515, the outer sleeve 1518 and the protective hood 1520 are in assembled configuration in which the protective hood 1520, the outer sleeve 1518 and the shaft portion 1515 are connected together along their longitudinal axes as shown. The shaft portion 1515 is connected to the first control member 1610 of the hand piece 1514 and when the first control member 1610 is rotated, the shaft portion 1515, the outer sleeve 1518 and the protective hood 1520 also rotates axially. Thus, a user can change and control the direction of the protective hood 1520 opening exposing the burr bit 1530 by manipulating the first control member 1610.

A second control member 1620, also provided in the hand piece 1514, is operably connected to the flexible neck portion 1517. When the second control member 1620 is pushed in the direction shown by the arrow E, the distal end (where the protective hood 1520 is) of the surgical instrument 1500 bends toward the ventral side V of the instrument. The distal end of the instrument in the bent position is illustrated by the dotted outline 1520A. The details of the structures comprising the flexible neck portion 1517 and examples of structural arrangement between the second control member 1620 and the flexible neck portion 1517 that enables this controlled bending or flexing of the distal end of the surgical instrument 1500 will be described further below.

Figure 16B:
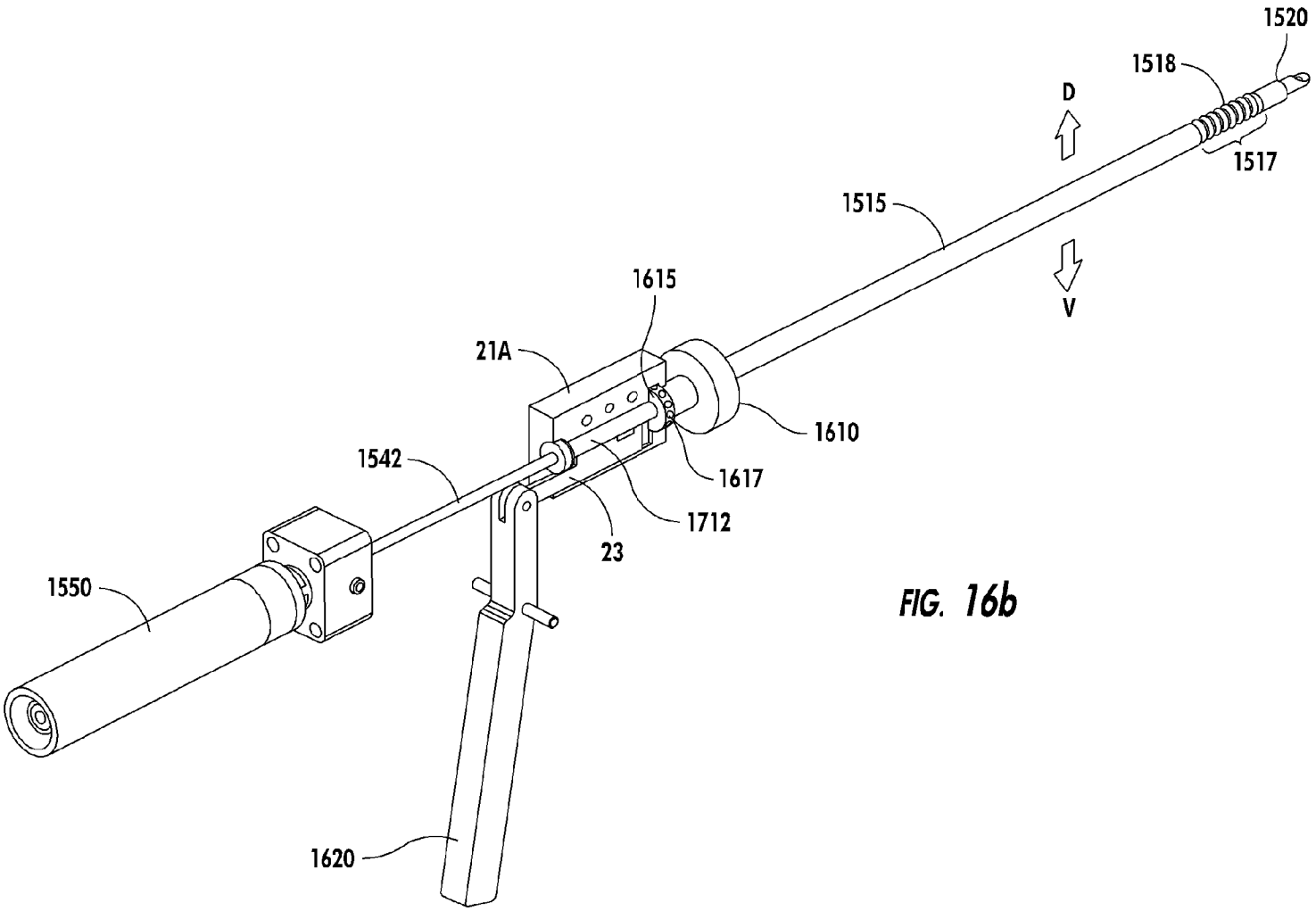

In FIG. 16b, another partial assembly view of the surgical instrument 1500 is shown without the bearing block 21B and the other half 20A of the main body of the hand piece 1514. The first control member 1610 is configured with a detent wheel 1615 that extends into and engage the bearing blocks 21A and 21B. The detent wheel 1615 allows incrementally stepped rotation of the first control member 1610 which, in turn, allows controlling the rotation of the protective hood 1520 in incremental steps.

The detent wheel 1615 can be configured and adapted so that the incremental steps can be of a desired size. The incrementally steps can be achieved by a variety of appropriate engagement structure between the detent wheel 1615 and the bearing blocks 21A and 21B. For example, the detent wheel 1615 in this example is provided with a plurality of spring loaded detents 1617 along its periphery which engage the corresponding notches (not shown) provided in the bearing blocks 21A and 21B.

Alternatively, the wheel 1615 can be configured and adapted to rotate within the bearing blocks 21A and 21B under certain amount of friction so that the first control member 1610 can be turned by the user but prevents free rotation of the first control member 1610.

Figure 17A:
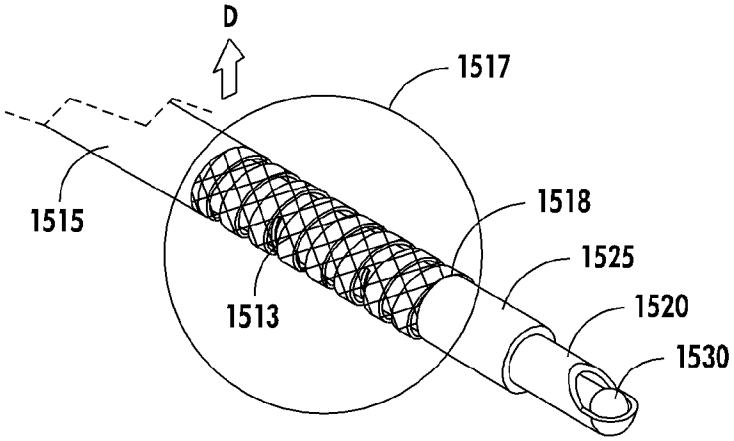
FIG. 17a is a detailed view of the flexible neck portion 1517 of the surgical instrument 1500 from the dorsal side D of the surgical instrument 1500.
Figure 17B:
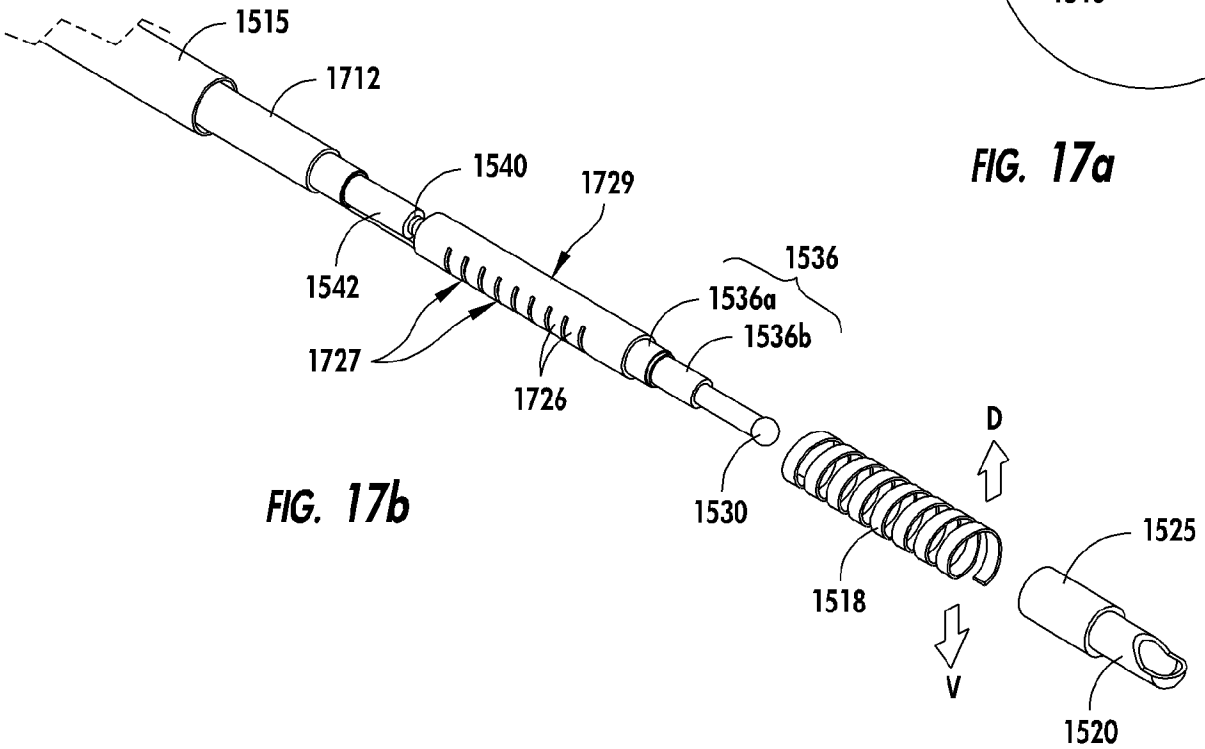

FIGS. 17a and 17b illustrate the detailed structures that comprise the flexible neck portion 1517 viewed from the dorsal side D of the surgical instrument 1500. FIG. 17a shows the flexible neck portion 1517 in fully assembled form and FIG. 17b shows an exploded view of the flexible neck portion 1517 and its components. The surgical tool bit 1530 which is connected to the drive shaft 1542 and resides within the protective hood 1520 in fully assembled configuration. The protective hood 1520 has a base portion 1525 and the outer sleeve 1518 connects the distal end of the shaft portion 1515 and the base portion 1525 of the protective hood 1520. The outer sleeve 1518 in one preferred embodiment has a coil structure made of a suitable material that can resiliently bend. The outer sleeve 1518 can be made of metal alloys (e.g. surgical stainless steel), plastic, or composite materials having suitable properties for the application. The outer sleeve 1518 is attached to the shaft portion 1515 and the base portion 1525 by a suitable method (welding, adhesive bonding, ultrasonic bonding, etc.) to allow the shaft portion 1515, the outer sleeve 1518 and the protective hood 1520 assembly to rotate as one unit when the user turns the shaft portion 1515 using the first control member 1610. A protective wrapping 1513 can be wrapped around the outer sleeve 1518. The protective wrapping 1513 can have a wire mesh structure and can be made of metal wires or polymer fibers as appropriate.

The mesh structure 1513 is bonded to the outer sleeve 1518 and the base portion 1525 of the protective hood 1520. The mesh can be metal wire mesh or plastic wire mesh or synthetic fiber mesh that has appropriate strength and surface characteristics to provide a protective covering. The mesh structure 1513 protects the device structures in the flexible neck portion 1517 and also protects the surrounding tissues while the instrument 1500 is being used in surgical procedure.

Inside the outer sheath formed by the shaft portion 1515, outer sleeve 1518 and the protective hood 1520, resides the inner shaft 1712 which is attached to the hand piece 1514 at its proximal end and extends through the shaft portion 1515. The distal end of the inner shaft 1712 is configured to be attached to the inner sleeve 1720. The inner shaft 1712 is configured to have a length so that the inner sleeve 1720 and the outer sleeve 1518 are in longitudinal alignment as shown in FIG. 17a. The distal end of the inner shaft 1712 can be configured with a sleeve 1713 that receives the inner sleeve 1720.

At the distal end of the inner sleeve 1720, spacers 1536a and 1536b form a spindle housing 1536. The flexible drive shaft 1540 extends through the spindle housing 1536 and connects with the spindle 1531 of the surgical tool bit 1530. The spindle 1531 and the flexible drive shaft 1540 is appropriately journaled within the spindle housing 1536 to rotate therein. The spindle housing 1536 is appropriately sized to fit in the space between the base portion 1525 of the protective hood 1520 and the spindle 1531 of the surgical tool bit 1530. The spindle housing 1536 keeps the spindle of the surgical tool bit 1530 aligned in the longitudinal center of the shaft assembly and also can function as bearings allowing the surgical tool bit 1530 to spin within the shaft assembly.

Figures 18A, 18B:
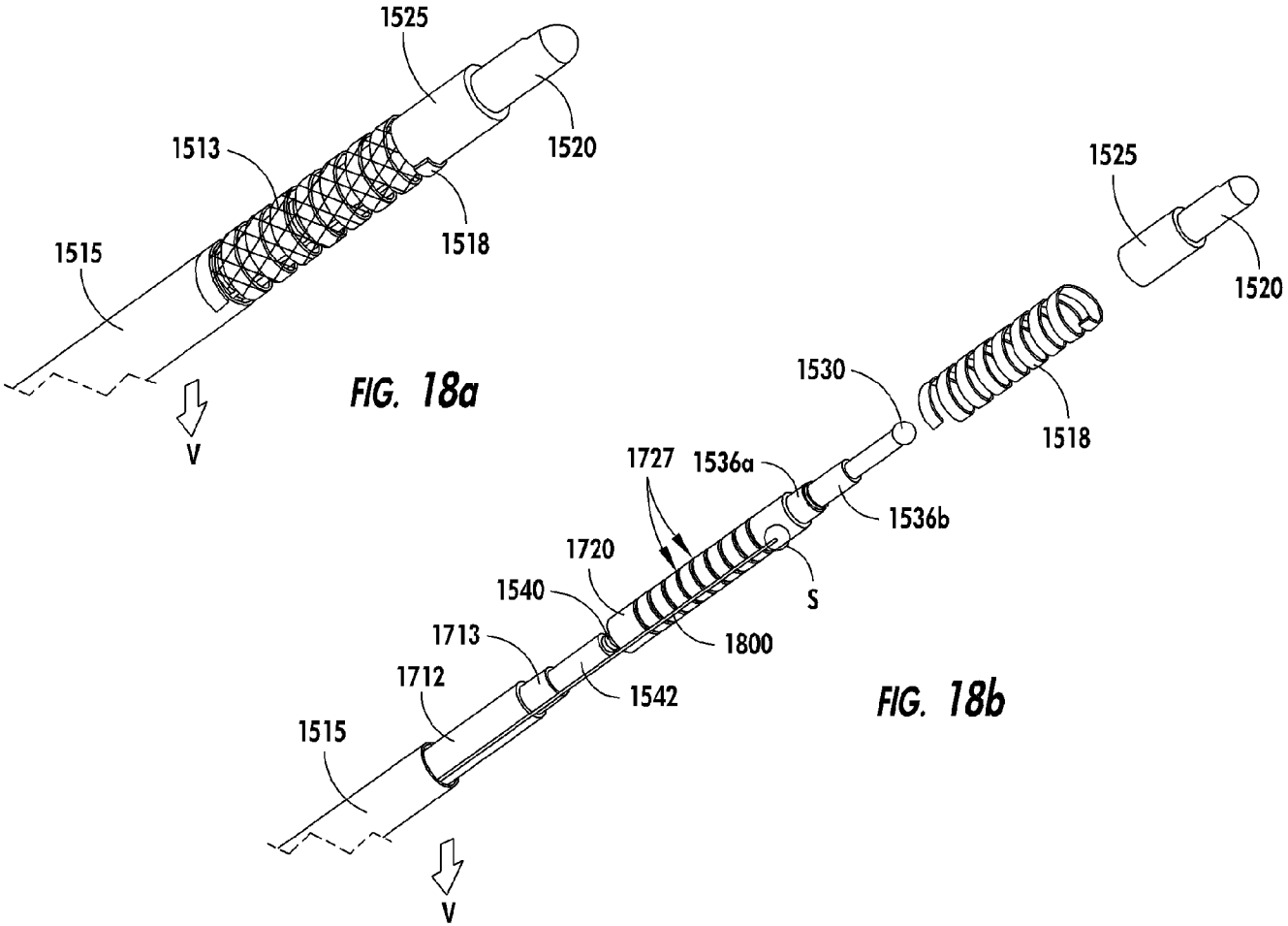
Figure 21A:
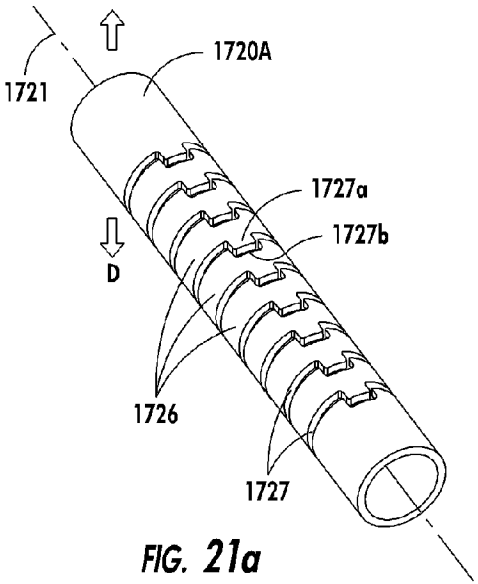
FIG. 21a-21d show various views of one embodiment of the inner sleeve 1720 forming the flexible neck portion 1517.
Figure 21B:
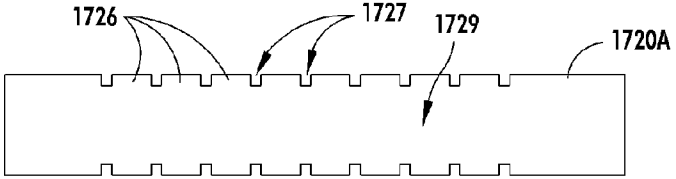

The inner sleeve 1720 is provided with a plurality of slots 1727 that are oriented substantially transverse to the longitudinal axis 1721 (see FIGS. 21a and 21c) of the inner sleeve 1720. The slots 1727 are cut from the ventral side V of the inner sleeve 1720 and traverse laterally into the inner sleeve 1720 but not completely through it so that a portion of the inner sleeve 1720 is intact along its length along the dorsal side D of the inner sleeve 1720. This intact region forms a spine 1729 of the inner sleeve 1720 along its length on the dorsal side D. The plurality of slots 1727 define a rib portion 1726 between two adjacent slots 1727. The slots 1727 allow the inner sleeve 1720 to be bent preferentially toward its ventral side V. The inner sleeve 1720 bends until the rib portions 1726 contact one another and, thus, the width of the plurality of slots 1727 determines how much the inner sleeve 1720 can bend and how much force is required to bend the inner sleeve 1720. The substantially transverse slots 1727 do not have to be perpendicular to the longitudinal axis of the inner sleeve 1720. They just need to be in substantially transverse orientation to allow the inner sleeve 1720 to bend. The orientation of the plurality of slots 1727 can be from about 10° to 90° from the longitudinal axis of the inner sleeve 1720. Preferably, the inner sleeve 1720 is made of a material that has sufficient elasticity to bend resiliently while having sufficient toughness to survive the cyclical stress imposed on it by repeated bending the inner sleeve 1720 can experience during the life of the surgical instrument 1500. The inner sleeve 1720 can be made of metal alloys, polymers, composites, etc. An FIGS. 18a and 18b illustrate the detailed structures that comprise the flexible neck portion 1517 viewed from the ventral side V of the surgical instrument 1500. FIG. 18a shows the flexible neck portion 1517 in fully assembled form and FIG. 18b shows an exploded view of the flexible neck portion 1517 and its components.

The ventral side view of FIG. 18b shows a pull wire 1800 that operably connects the inner sleeve 1720 to the second control member 1620 of the hand piece 1514 for controlling the bending of the flexible neck portion 1517. In this embodiment, the pull wire 1800 runs along the ventral side V of the inner sleeve 1720 in the space between the shaft portion 1515 and the inner shaft 1712. Within the flexible neck portion 1517, the pull wire 1800 runs along the space between the inner sleeve 1720 and the outer sleeve 1518. The distal end of the pull wire 1800 is secured to the inner sleeve 1720 at a spot S near the distal end of the inner sleeve 1720. The pull wire 1800 can be attached to the spot S by any appropriate means such as welding, adhesive bonding, ultrasonic bonding, etc. depending upon the particular material selection for the inner sleeve 1720. The pull wire 1800 itself in a preferred embodiment is formed of a high tensile strength metal alloy wire for its durability. An example of such wire is austenitic steel wire. A composite or polymer-based cable can also be used.

In use, when the pull wire 1800 is pulled towards the proximal end (the end attached to the hand piece 1514) the gaps formed by the plurality of slots 1727 along the ventral side V of the inner sleeve 1720 are squeezed closed along the ventral side V of the inner sleeve 1720 and causes the inner sleeve 1720 to bend toward the inner sleeve's ventral side V. As mentioned above, by adjusting the width of the plurality of slots 1727, the amount of bend in the flexible neck portion 1517, measured by the radius of curvature of the bend in the flexible neck portion 1517, can be adjusted. Generally, wider slots 1727 result in smaller radius of curvature of the bend (i.e. sharper bend) and narrower slots 1727 result in larger radius of curvature of the bend (i.e. shallower or gentler bend).

Figure 19:
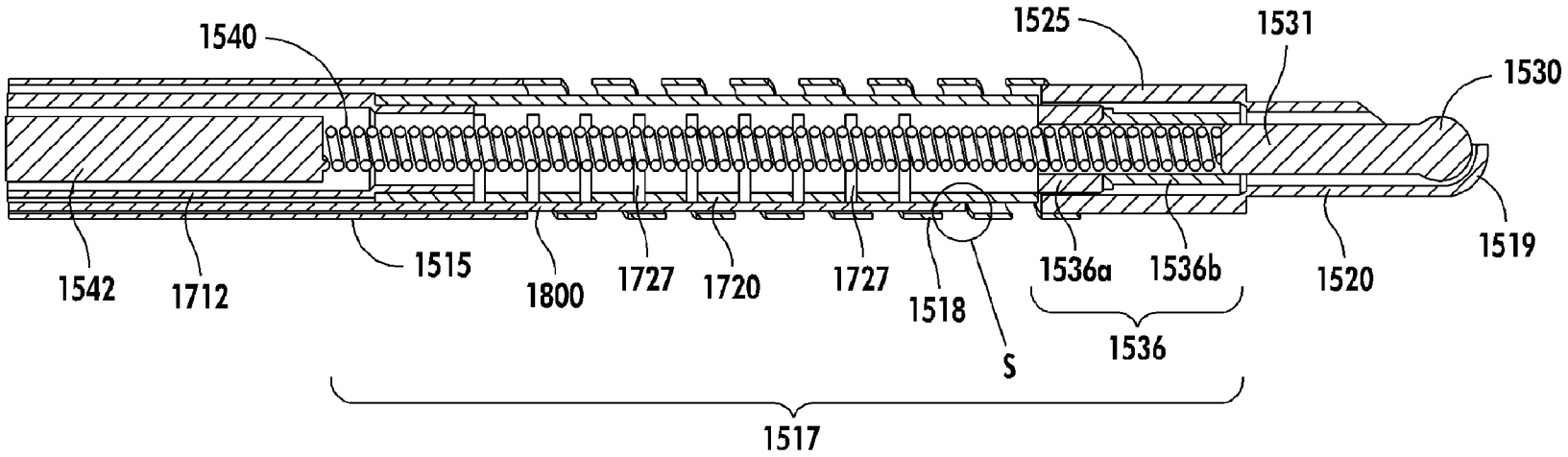
FIG. 19 is a longitudinal cross-sectional view of the flexible neck portion 1517 of the surgical instrument 1500.

FIG. 19 is a longitudinal cross-section of the flexible neck portion 1517 showing further details of the arrangement of the components that form the flexible neck portion 1517. The shaft portion 1515, the outer sleeve 1580 and the protective hood 1520 are connected together in longitudinal arrangement as discussed above and forms the outer-most structure of the flexible neck portion 1517. The inner sleeve 1720 is shown disposed within the outer sleeve 1518 and connected to the inner shaft 1712 as discussed earlier. The drive shaft 1542 and the surgical tool bit 1530 are connected by a flexible second drive shaft 1540. The combination of the drive shaft 1541 and the flexible second drive shaft 1540 will be referred to hereinafter as the "drive shaft assembly." The drive shaft assembly is disposed within the inner shaft 1712 and inner sleeve 1720 and extends therethrough so that the second drive shaft 1540 is disposed within the inner sleeve 1720 and the surgical tool bit 1530 is disposed within the protective hood 1520. Thus, the second drive shaft 1540 bends along with the inner sleeve 1720 while transmitting the rotational torque from the drive shaft 1542 to the surgical tool bit 1530. In a preferred embodiment shown, the second drive shaft 1540 is a flexible coil-type drive shaft.

The pull wire 1800 is shown extending between the inner sleeve and the outer sleeve along the ventral side V of the surgical instrument 1500. The pull wire 1800 is attached to a spot S near the distal end of the inner sleeve 1720.

Figure 20B:
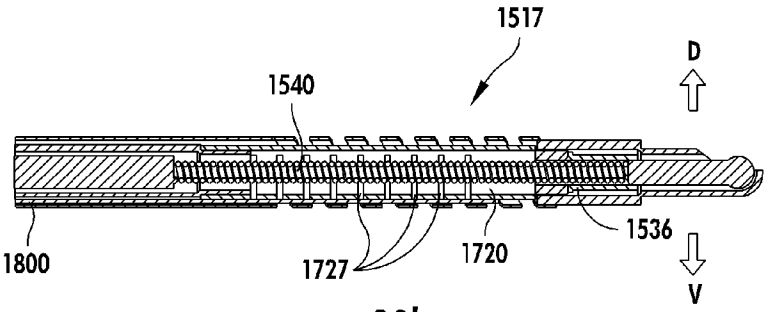
FIG. 20a-20c are longitudinal cross-sectional views showing the details of the operation of the articulation wire 1800 in controllably bending the flexible neck portion 1517 of the surgical instrument 1500.
Figure 20C:
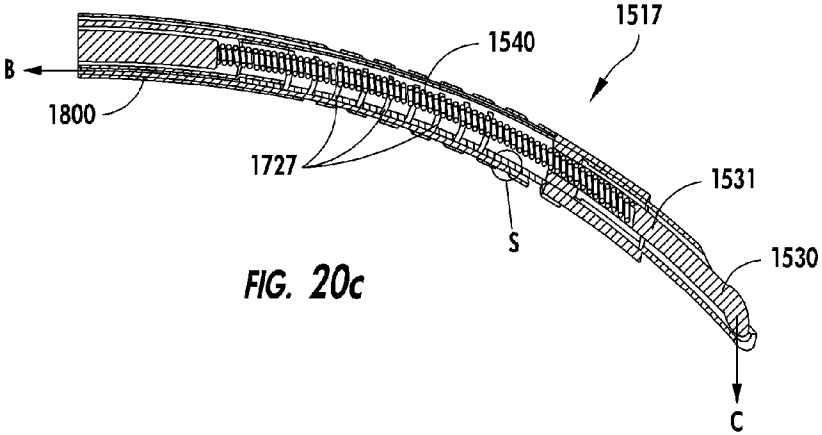
Figure 20A:
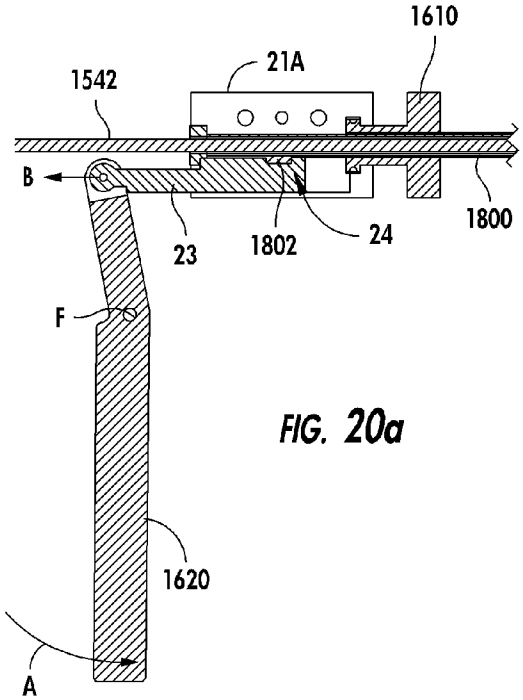

FIG. 20a shows a cross-sectional detailed view of the arrangement between the second control member 1620 and the pull wire 1800 at the wire's proximal end. This is an example of the structure showing how the pull wire 1800 is operably connected to the second control member 1620 so that the bending of the flexible neck portion 1517 can be controlled by manipulation of the second control member 1620. The second control member 1620 is configured as a lever with a fulcrum F positioned between its first and second ends. A linkage member 23 connects the proximal end 1802 of the pull wire 1800 to the first end of the second control member 1620. When a user pushes the second end of the second control member 1620 in the direction shown by the arrow A, the lever structure pivots about its fulcrum and the second end of the second control member 1620 pulls on the linkage member 23 and thus the pull wire 1800 in the direction shown by arrow B. As described above, when the pull wire 1800 is pulled by the manipulation of the second control member 1620, the pull wire 1800 pulls on the distal end of the inner sleeve 1720 causing the inner sleeve 1720 and, in turn, the flexible neck portion 1517 to bend toward the ventral side as shown in FIG. 20c.

Figure 21C:
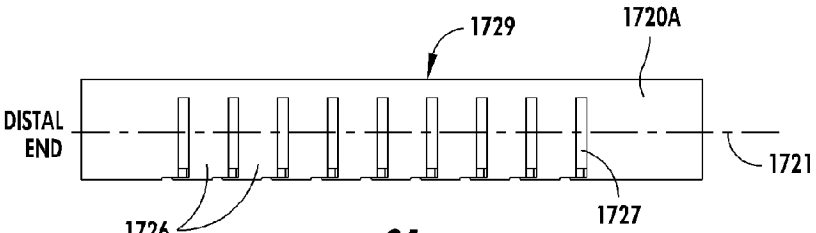
Figure 21D:
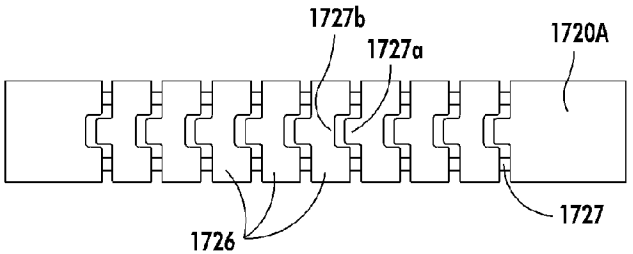
Figure 22A:
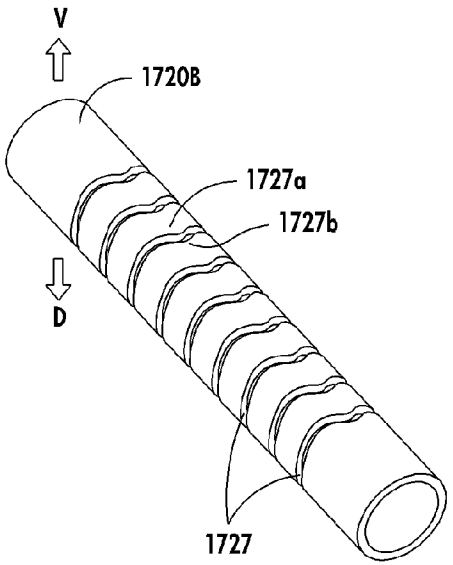
FIG. 22a-22d show various views of another embodiment of the inner sleeve 1720 forming the flexible neck portion 1517.
Figure 22B:
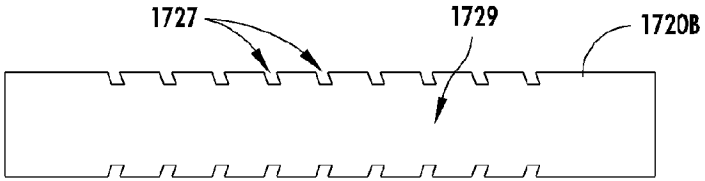
Figure 22C:
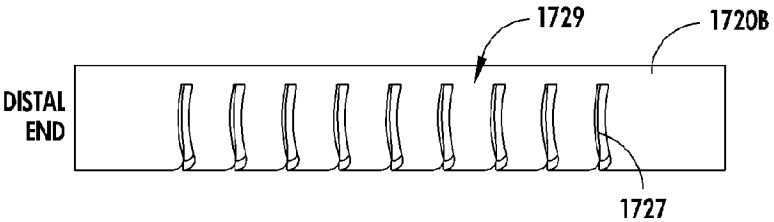
Figure 22D:
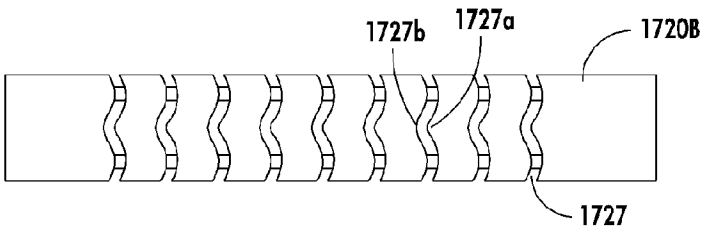

FIGS. 21a-21d show an inner sleeve 1720A in detail according to one embodiment. As described above in reference to the inner sleeve 1720, the inner sleeve 1720A has a plurality of substantially transverse slots 1727 that extend partially through the inner sleeve 1720A from its ventral side V toward the dorsal side D. The slots 1727 do not extend completely through the inner sleeve 1720A and a spine 1729 is left intact along the dorsal side D of the inner sleeve 1720A as shown in FIG. 21c. To prevent or minimize any torsional twisting when the inner sleeve 1720A is bent toward its ventral side V, each of the plurality of slots 1727 in the inner sleeve 1720A are shaped to provide interference between two adjacent rib portions 1726. In the example shown, the slots 1727 are shaped so that the rib portions 1726 have a square shaped protruding tab 1727a and a corresponding square-shaped notche 1727b along the ventral side V of the inner sleeve 1720. The protruding tabs 1727a extend partially into an adjacent notch 1727b providing interference and prevent the inner sleeve 1720A from twisting. The particular shape of the protruding tabs 1727a and the corresponding notches 1727b are not limited to the square shaped example. Any variations that are suitable for preventing torsional twisting can be implemented. For example, FIGS. 22a-22d show an inner sleeve 1720B according to another embodiment. In this embodiment, the protruding tabs 1727a and the corresponding notches 1727b are configured to have a chevron-like shape.

In the embodiment of the surgical instrument 1500 shown in FIG. 14a-20c, one preferred example of the actuating means for controllably bending the flexible neck portion provided within the inner sleeve and the inner shaft was illustrated. That example of an actuating means included a pull wire 1800 actuator for delivering the mechanical force necessary to bend the flexible neck portion 1517. The actuating means, however, can be enabled by a number of other arrangements that are available in the art.

Figure 23:
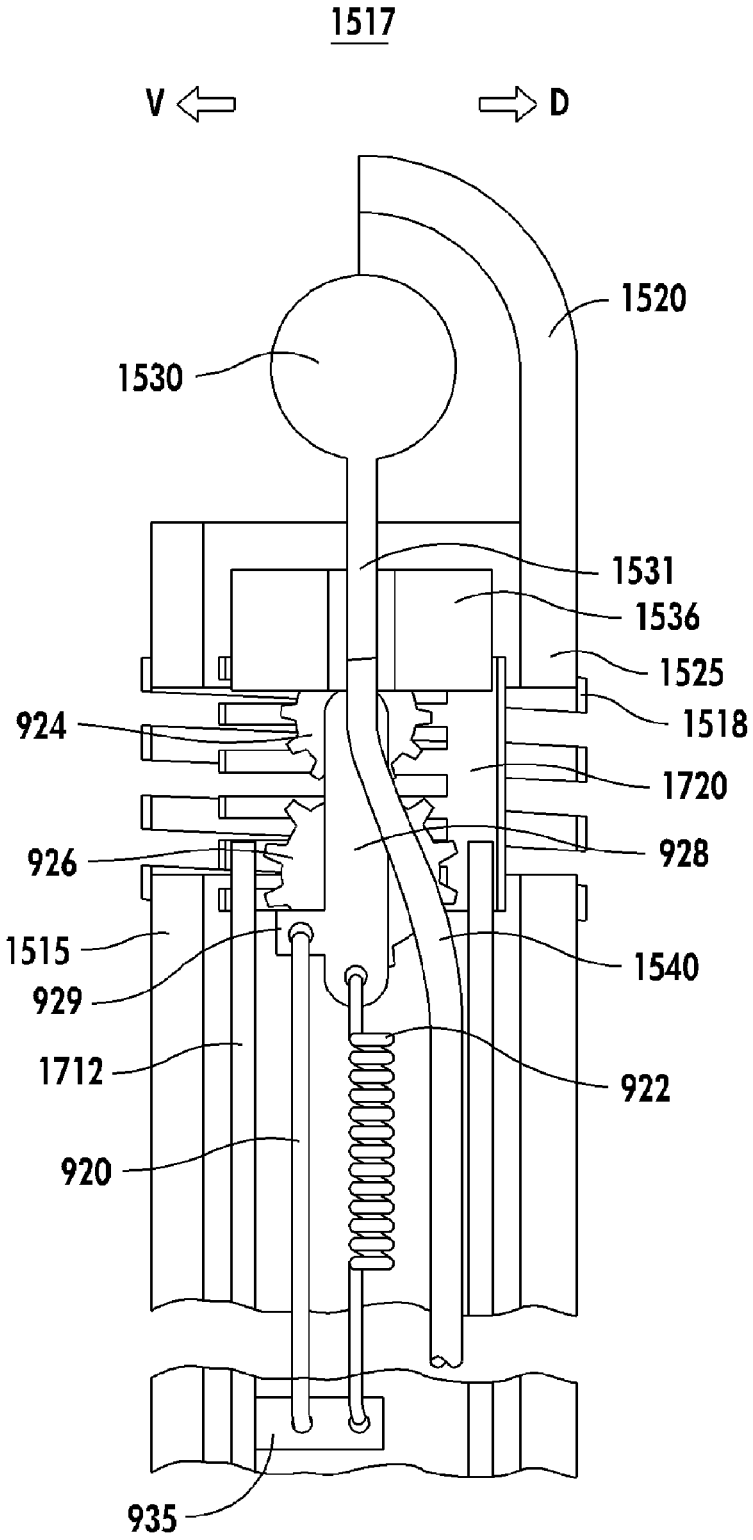
FIGS. 23-26b are longitudinal cross-sectional views of the flexible neck portion 1517 illustrating the various other embodiments of actuating means for controllably bending the flexible neck portion.

FIG. 23 shows an example of the flexible neck portion 1517 in which a shape memory alloy based actuator 920 ("SMA actuator") for actuating the bending of the flexible neck portion 1517 is employed. In this embodiment, the SMA actuator 920 is used to create an electrically actuated linkage between the protective hood 1520 and the shaft 1515.

A planetary gear system comprising a planet gear 924 and a sun gear 926 is disposed within the inner sleeve 1720 and connects the distal end of the inner shaft 1712 and the tool-bit spindle housing 1536. The sun gear 926, which is the stationary gear in the gear system, is attached to the distal end of the inner shaft 1712 and the planet gear 924, the gear that rotates around the sun gear 926, is attached to the spacer 1536 at the distal end of the inner sleeve 1720. An appropriately configured bracket 928 connects the axles of the two gears 924 and 926. An antagonistic pair of a coil spring 922 and the SMA actuator 920 are provided in the configuration shown to actuate and control the bending of the flexible neck portion 1517.

A lever portion 929 is provided on the bracket 928 and extends toward the ventral side V. The SMA actuator 920 is attached to the lever portion 929 and extends longitudinally within the inner shaft 1712 toward the proximal end of the inner shaft 1712 and affixed/anchored to an appropriate anchoring portion 935 inside the inner shaft 1712. The coil spring 922 is attached to the bracket 928 and extends longitudinally within the inner shaft 1712 toward the proximal end of the inner shaft 1712. The coil spring 922 in a stretched state is also affixed/anchored to the anchoring portion 935 inside the inner shaft 1712. The coil spring 922 provides an opposing tension that pulls on the planet gear 924, via the bracket 928, keeping the planet gear 924 in the neutral position (i.e. the flexible neck portion 1517 is straight) shown.

The SMA actuator 920 can be made from super-elastic nickel titanium shape memory alloy that can be elastically deformed or strained at room temperature and is preconditioned to return to an original state from the deformed state when heated. In the embodiment of FIG. 23, the SMA actuator 920 is in its deformed state where the opposing tension force of the coil spring 922 is pulling on the SMA actuator 920 and keeping the flexible neck portion 1517 in the straight configuration shown. The SMA actuator 920 is configured as an electroactive, resistive element in a circuit that can apply a desired electrical current when the second control member 1620 in the hand piece 1514 is pressed. Because the SMA actuator 920 is a resistive element, the actuator heats up when electrical current is applied through it and the resulting heat causes the SMA actuator 920 to return to its original state. In this embodiment, the SMA actuator 920 is preconditioned so that in its original state, the SMA actuator 920 is shorter. Thus, when the SMA actuator 920 is heated, it contracts to its original state. The contraction provides force opposing the coil spring 922 and pulls the planet gear 924 towards the ventral side V. This makes the planet gear 924 to rotate about the sun gear 926 toward the ventral side V and bends the inner sleeve 1720 in the same manner as the pull wire 1800 does in the previous embodiment discussed above. When the electrical circuit is disconnected, the SMA actuator 920 cools down and returns to its original state returning the flexible neck portion 1517 to the straight position shown in FIG. 23.

Selection of different gear sets or gear ratios in the planetary gear system would allow for different bending angles and resolution. The flexible second drive shaft 1540 that drives the surgical tool bit 1530 can be routed as illustrated or other routing paths can be used as appropriate.

Figure 24:
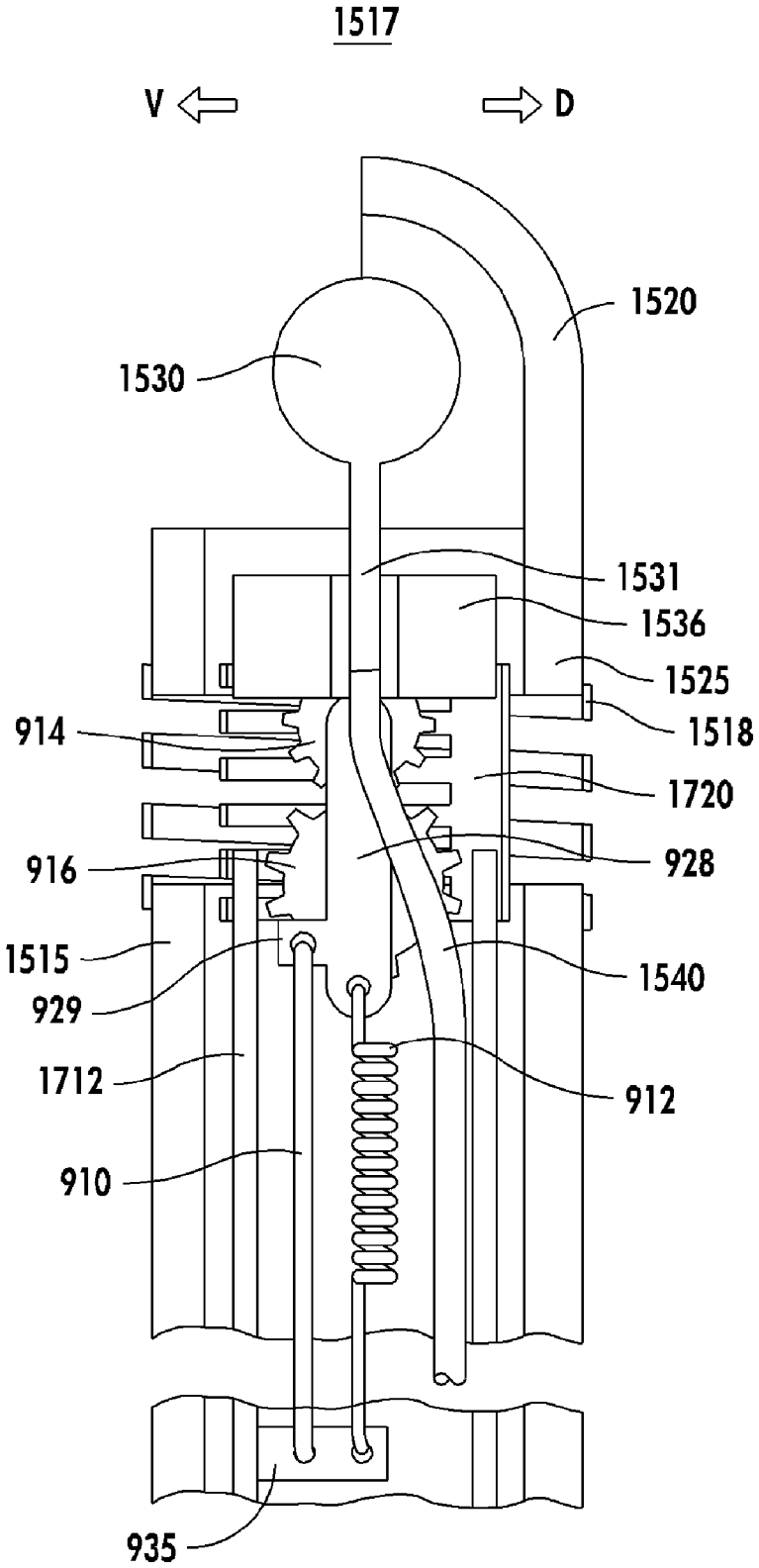

FIG. 24 shows an example of the flexible neck portion 1517 in which an electro-active polymer based actuator 910 for actuating the bending of the flexible neck portion 1517 is employed. In this embodiment, the electro-active polymer based actuator 910 is used to create an electrically actuated linkage between the protective hood 1520 and the shaft 1515. Electro-active polymers are similar to the shape memory metals in that they change shape or deform when electrically activated. When a voltage is applied to electrodes contacting a pre-strained polymer, the polymer deflects.

Similar to the configuration shown in FIG. 23, a planetary gear system comprising a planet gear 914 and a sun gear 916 is disposed within the inner sleeve 1720 and connects the distal end of the inner shaft 1712 and the spacer 1536. The sun gear 916 is attached to the distal end of the inner shaft 1712 and the planet gear 914 is attached to the spacer 1536 at the distal end of the inner sleeve 1720. An appropriately configured bracket 918 connects the axles of the two gears 914 and 916. Similar to the SMA actuator embodiment, an antagonistic pair of a coil spring 912 and an electro-active polymer based actuator 910 provide the actuating means for controllably bending the flexible neck portion 1517.

A lever portion 919 is provided on the bracket 918 and extends toward the ventral side V. The electro-active polymer based actuator 910 is attached to the lever portion 919 and extends longitudinally within the inner shaft 1712 toward the proximal end of the inner shaft 1712 and affixed/anchored to an appropriate anchoring portion 935 inside the inner shaft 1712. The coil spring 912 is attached to the bracket 918 and extends longitudinally within the inner shaft 1712 toward the proximal end of the inner shaft 1712. The coil spring 912 in a stretched state is also affixed/anchored to the anchoring portion 935 inside the inner shaft 1712. The coil spring 912 provides an opposing tension that pulls on the planet gear 914, via the bracket 918, keeping the planet gear 914 in the neutral position (i.e. the flexible neck portion 1517 is straight) shown.

Similar to the SMA actuator based embodiment of FIG. 23, the surgical instrument 1500 is configured to have electrical current flow through the electro-active polymer based actuator 910 through manipulation of the second control member 1620 in the hand piece 1514. When the electro-active polymer based actuator 910 is electrically activated, the polymer actuator 910 contracts and pulls the planet gear 914 to rotate about the sun gear 916 toward the ventral side V and bends the inner sleeve 1720 in the same manner as the pull wire 1800 does in the previous embodiment discussed above. When the electrical circuit is disconnected, the electro-active polymer actuator 910 returns to its original state returning the flexible neck portion 1517 to the straight position shown in FIG. 24.

As with the embodiment of FIG. 23, selection of different gear sets or gear ratios in the planetary gear system would allow for different bending angles and resolution. The flexible second drive shaft 1540 that drives the surgical tool bit 1530 can be routed as illustrated or other routing paths can be used as appropriate.

Figure 25B:
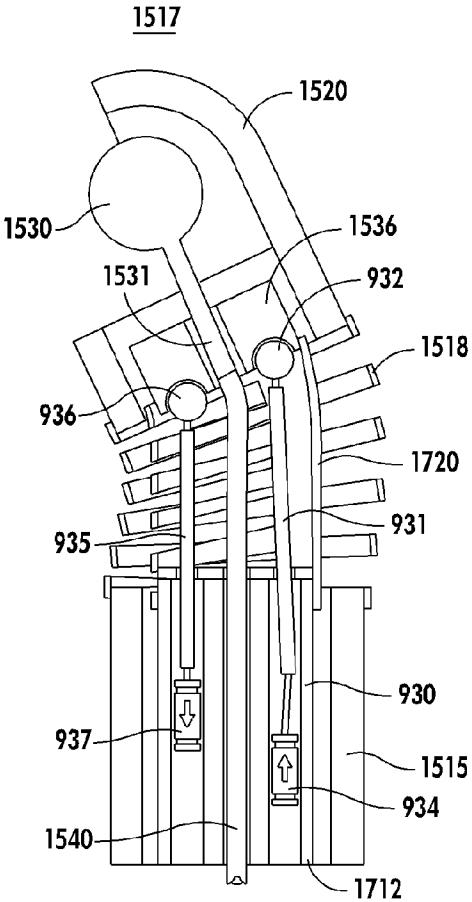
Figure 25A:
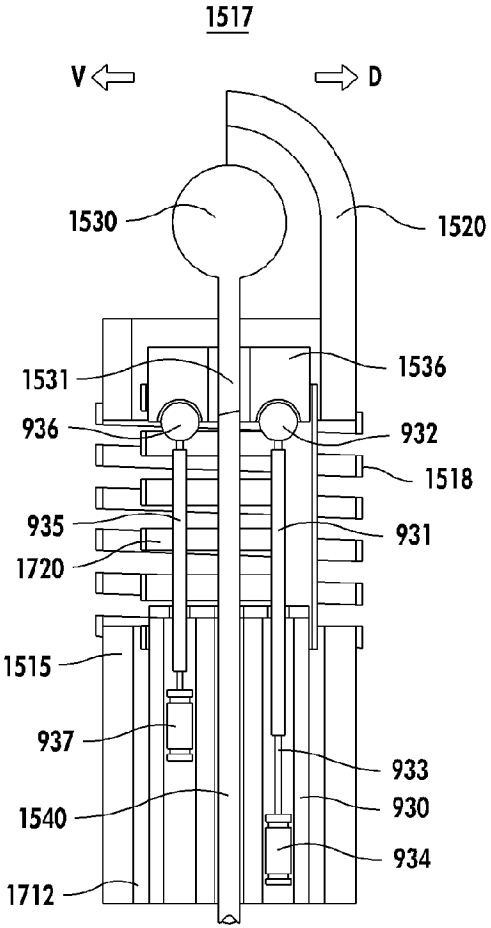

FIGS. 25a and 25b illustrate an example of the flexible neck portion 1517 in which a hydraulic piston driven actuator mechanism is employed as the actuating means for controllably bending the flexible neck portion. The hydraulic mechanism is provided within the inner sleeve 1720 and connects the spacer 1536 to the inner shaft 1712. The hydraulic mechanism comprises a pair of piston/rod assemblies. A first piston 934 and rod 931 form a first of the piston/rod assembly. A second piston 937 and rod 935 form a second of the piston/rod assembly. The distal ends of the first and second piston/rod assemblies are provided with ball joints 932, 936, respectively, and the ball joints are received in the spacer 1536. The spacer 1536 is provided with a centrally located bore through which the spindle of the surgical tool bit 1530 extends.

The distal end of the inner shaft 1712 forms an actuator block 930 for the hydraulic mechanism. The actuator block 930 comprises a pair of cylinders that receive the pistons 934, 937 of the first and second piston/rod assemblies. The hand piece 1514 of the surgical instrument 1500 is configured and adapted to feed compressed air up to the actuator block 930 in a controlled manner so that the position of the pistons 934, 937 in the cylinders of the actuator block 930 can be controlled.

Starting from the configuration shown in FIG. 25a in which the flexible neck portion 1517 is in straight configuration, by adjusting the compressed air to the two cylinders in the actuator block 930, the first piston 934 can be pushed up (i.e., toward distal end) while the second piston 937 can be pulled down (i.e., toward proximal end). This will cause the flexible neck portion 1517 to bend toward the ventral direction V as shown in FIG. 25b. The amount of the bend can be controlled and also straighten the flexible neck portion 1517 by controlling the respective motions of the pistons 934 and 937 within the actuator block 930.

Figure 26B:
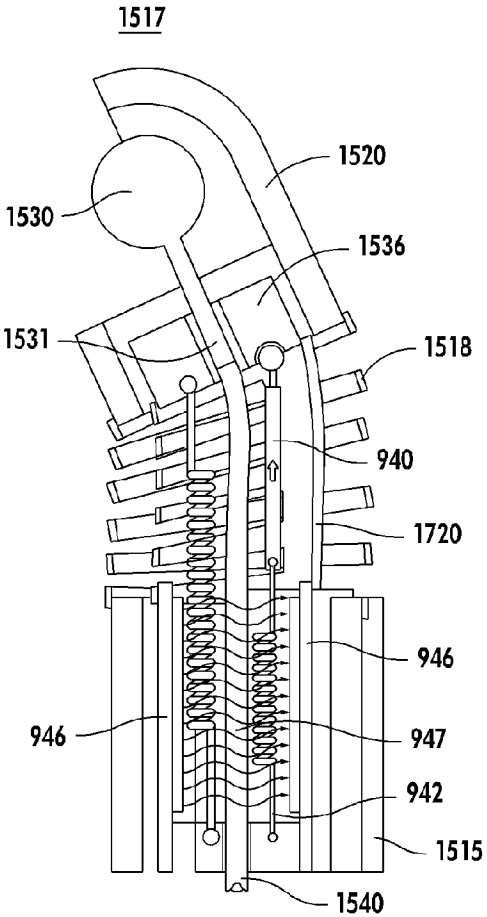
Figure 26A:
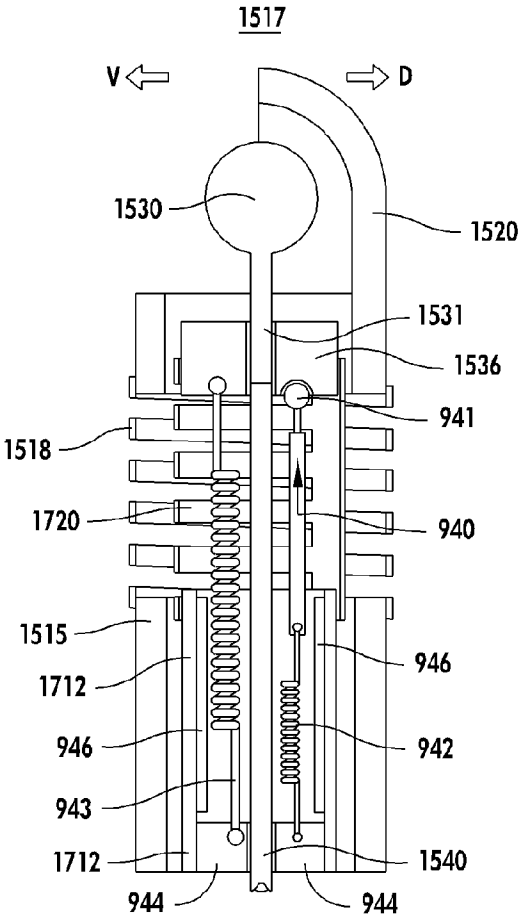

FIGS. 26a and 26b illustrate another example of the flexible neck portion 1517 in which a magnetic shape memory actuator mechanism is employed as the actuating means for controllably bending the flexible neck portion. Similar to some of the other actuating mechanisms discussed above, an antagonistic pair of a coil spring 943 and a magnetic shape memory actuator 940 is utilized for controlling the bending of the flexible neck portion. The coil spring 943 is provided on the ventral side V within the inner sleeve 1720. The distal end of the coil spring 943 is connected to the spacer 1536 and the proximal end of the coil spring 943 is connected to the inner shaft 1712. The inner shaft 1712 can be provided with a tab 944 or a similar structure to accommodate this attachment. The magnetic shape memory actuator 940 is provided on the dorsal side D within the inner sleeve 1720. The distal end of the magnetic shape memory actuator 940 is attached to the spacer 1536 via a ball joint 941 to allow angular displacement between the spacer 1536 and the magnetic shape memory actuator 940. The proximal end of the magnetic shape memory actuator 940 is attached to the inner shaft 1712 via a tab 944 or a similar structure. In another embodiment, a second spring member 942 connects the proximal end of the magnetic shape memory actuator 940 to the inner shaft 1712. The second spring member 942 at rest state shown in FIG. 26a is not in fully compressed state and can moderate the initial actuation motion of the magnetic shape memory actuator 940 to provide smoother take off motion.

Provided on the inside wall surface of the inner shaft 1712 are electromagnets 946 for activating the magnetic shape memory actuator 940. When the electromagnets 946 are turned on and magnetic field 947 is established between the electromagnets 946 the magnetic shape memory actuator 940 expands and push the dorsal side of the spacer 1536 up while the coil spring 943 contracts and pulls down on the ventral side of the spacer 1536 bending the flexible neck portion 1517 as shown in FIG. 26b. When the magnetic field 947 is removed by turning the electromagnets 946 off, the magnetic shape memory 940 returns to its original shape and straighten the flexible neck portion 1517. The electricity required for activating the electromagnets 946 can be provided with batteries in the hand piece 1514 or from an external power source and the second control member 1610 can be configured to be the on/off switch. The spacer 1536 is provided with a centrally located bore through which the spindle of the surgical tool bit 1530 extends.

One example of magnetically controlled shape memory material is Ni—Mn—Ga alloy. When the magnetic shape memory actuator 940 is subjected to a magnetic field the proportions of the variants change resulting in the shape change of the element.

FIGS. 27a and 27b show detailed views of the distal end of an embodiment of the surgical instrument 1500 that is configured and adapted to be used for soft tissue resections. The surgical tool bit in this embodiment is a soft tissue resector bit 1330. The soft tissue resector bit 1330 has a hollow structure and comprises an inner cutting aperture 1330A on one side defined by an inner cutting edge 1330C. The protective hood 1519 has an opening, an outer cutting aperture 1519A, on one side that is defined by an outer cutting edge 1519C. At least portions of the inner cutting edge 1330C and the outer cutting edge 1519C are machine sharpened for cooperating with each other for shearing tissue to be removed from the patient. The soft tissue resector bit 1330, driven by the flexible second drive shaft 1540, freely rotates or is journaled within the protective hood 1519 and permits the inner cutting edge 1330C to cooperate with the outer cutting edge 1519C to sever tissue as the soft tissue resector bit 1330 rotates. Any tissue entering the outer cutting opening 1519A will be sheared by the cooperating motion of the cutting edges.

The surgical instrument in this embodiment is configured and adapted to remove the severed tissue debris through the instrument. In one embodiment, through the hollow interior of the soft tissue resector bit 1330 can be provided means for delivering vacuum to suck out the tissue debris. Preferably, a means for delivering irrigation fluid is also provided through the hollow interior of the soft tissue resector bit 1330. In the example shown, a flexible tubular member 1332, configured to have two channels, a vacuum delivery channel 1334 and an irrigation fluid delivery channel 1335, is provided through the hollow interior of the soft tissue resector bit 1330. The tubular member 1332 preferrably extends within and through the flexible second drive shaft 1540, and inner shaft 1712 to the proximal end of the surgical instrument 1500 to be in fluid communication with a vacuum source (not shown) to convey the removed tissue debris. The tubular member 1332 is also in fluid communication with an irrigation fluid source (not shown) at the proximal end of the surgical instrument 1500 for providing the irrigation fluid.

While the foregoing invention has been described with reference to the above embodiments, various modifications and changes can be made without departing from the spirit of the invention. Accordingly, all such modifications and changes are considered to be within the scope of the appended claims.

What is claimed is:

1. A surgical instrument comprising:

a hand piece having a distal end and a proximal end;

a shaft portion extending from the distal end of the hand piece and having a distal end and a proximal end;

a drive shaft disposed for rotation within the shaft portion, the drive shaft having a distal end and a proximal end thereof;

a surgical tool bit connected to the distal end of the drive shaft;

a protective hood connected to the distal end of the shaft portion, wherein the surgical tool bit resides within the protective hood, partially exposed, and the protective hood is rotatable relative to the surgical tool bit exposing a different portion of the surgical tool bit; and said hand piece including a first control member, said first control member operably connected to the proximal end of the shaft portion and manipulation of the first control member controls the rotation of the protective hood relative to the hand piece and the drive shaft via the shaft portion,

*wherein the flexible neck portion is operably connected to the hand piece and the flexible neck portion's bending motion is actuated and controlled from the hand piece.*

2. The surgical instrument of claim 1, wherein the surgical tool bit is a bone removing bit.

3. The surgical instrument of claim 1, wherein the surgical tool bit is a soft tissue resector bit and the surgical instrument is configured and adapted to remove soft tissue debris through the instrument.

4. The surgical instrument of claim 3, wherein said soft tissue resector bit has a hollow interior and the surgical instrument further comprising a flexible tubular member provided through the hollow interior of the soft tissue resector bit, wherein said flexible tubular member comprises an irrigation fluid delivery channel for delivering irrigation fluid and a vacuum delivery channel for removing soft tissue debris.

5. The surgical instrument of claim 1, wherein the protective hood includes a dissecting foot plate portion.

6. The surgical instrument of claim 1, wherein the dissecting foot plate portion has a length of about 1 to 8 mm.

7. The surgical instrument of claim 1, further comprising a flexible neck portion connecting the protective hood to the distal end of the shaft portion, wherein the drive shaft comprises a flexible drive shaft portion at the distal end thereof and extending through the flexible neck portion to connect to the surgical tool bit.

[8. The surgical instrument of claim 7, wherein the flexible neck portion is operably connected to the hand piece and the flexible neck portion's bending motion is actuated and controlled from the hand piece.]

9. The surgical instrument of claim [8] *1*, wherein the flexible neck portion is configured and adapted to preferentially bend in one direction.

10. The surgical instrument of claim 9, wherein the flexible neck portion further comprising an actuation mechanism for controllably bending the flexible neck portion.

11. The surgical instrument of claim 10, wherein the actuating means is operably connected to the hand piece and the bending of the flexible neck portion is controlled by actuating the actuation mechanism from the hand piece.

12. A surgical instrument comprising:

a hand piece having a distal end and a proximal end;

a power drive mechanism provided with the hand piece;

a shaft portion extending from the distal end of the hand piece and having a distal end and a proximal end;

a drive shaft disposed for rotation within the shaft portion, the drive shaft having a distal end and a proximal end thereof, wherein the proximal end is connected to the power drive mechanism;

a surgical tool bit connected to the distal end of the drive shaft;

a protective hood attached to the distal end of the shaft portion, wherein the surgical tool bit resides within the protective hood, partially exposed, and the protective hood is rotatable relative to the surgical tool bit exposing a different portion of the surgical tool bit; and said hand piece including a first control member, said first control member operably connected to the proximal end of the shaft portion and manipulation of the first control member controls the rotation of the protective hood relative to the hand piece and the drive shaft via the shaft portion,

*wherein the flexible neck portion is operably connected to the hand piece and the flexible neck portion's bending motion is actuated and controlled from the hand piece.*

13. The surgical instrument of claim 12, wherein the surgical tool bit is a bone removing bit.

14. The surgical instrument of claim 12, wherein the surgical tool bit is a soft tissue resector bit and the surgical instrument is configured and adapted to remove soft tissue debris through the instrument.

15. The surgical instrument of claim 12, wherein said soft tissue resector bit has a hollow interior and the surgical instrument further comprising a flexible tubular member provided through the hollow interior of the soft tissue resector bit, wherein said flexible tubular member comprises an irrigation fluid delivery channel for delivering irrigation fluid and a vacuum delivery channel for removing soft tissue debris.

16. The surgical instrument of claim 12, wherein the protective hood includes a dissecting foot plate portion.

17. The surgical instrument of claim 12, wherein the dissecting foot plate portion has a length of about 1 to 8 mm.

18. The surgical instrument of claim 12, further comprising a flexible neck portion connecting the protective hood to the distal end of the shaft portion, wherein the drive shaft comprises a flexible drive shaft portion at the distal end thereof and extending through the flexible neck portion to connect to the surgical tool bit.

[19. The surgical instrument of claim 18, wherein the flexible neck portion is operably connected to the hand piece and the flexible neck portion's bending motion is actuated and controlled from the hand piece.]

20. The surgical instrument of claim [19] *12*, wherein the flexible neck portion is configured and adapted to preferentially bend in one direction.

21. The surgical instrument of claim 20, wherein the flexible neck portion further comprising an actuation mechanism for controllably bending the flexible neck portion.

22. The surgical instrument of claim 21, wherein the actuating means is operably connected to the hand piece and the bending of the flexible neck portion is controlled by actuating the actuation mechanism from the hand piece.

* * * * *